(12) United States Patent
Takato

(10) Patent No.: US 8,203,798 B2
(45) Date of Patent: Jun. 19, 2012

(54) OBJECTIVE OPTICAL SYSTEM

(75) Inventor: Hideyasu Takato, Shibuya-Ku (JP)

(73) Assignee: Olympus Medical Systems Corp., Tokyo (JP)

( * ) Notice: Subject to any disclaimer, the term of this patent is extended or adjusted under 35 U.S.C. 154(b) by 101 days.

(21) Appl. No.: 12/925,132

(22) Filed: Oct. 13, 2010

(65) Prior Publication Data

US 2011/0211267 A1    Sep. 1, 2011

Related U.S. Application Data

(63) Continuation of application No. PCT/JP2010/002514, filed on Apr. 6, 2010.

(30) Foreign Application Priority Data

Apr. 16, 2009 (JP) ................................. 2009-099935

(51) Int. Cl.
*G02B 13/04* (2006.01)
*G02B 9/14* (2006.01)

(52) U.S. Cl. ....................................... 359/753; 359/784

(58) Field of Classification Search .................. 359/749, 359/753, 784, 684, 689, 680
See application file for complete search history.

(56) References Cited

U.S. PATENT DOCUMENTS

| | | | | | |
|---|---|---|---|---|---|
| 5,805,359 | A | * | 9/1998 | Yamanashi | 359/753 |
| 2005/0219714 | A1 | * | 10/2005 | Nakayama | 359/749 |

FOREIGN PATENT DOCUMENTS

| | | |
|---|---|---|
| JP | 55-15005 | 4/1980 |
| JP | 61-44283 | 10/1986 |
| JP | 05-273459 | 10/1993 |
| JP | 06-317744 | 11/1994 |
| JP | 11-316339 | 11/1999 |
| JP | 2000-267002 | 9/2000 |
| JP | 2000-330015 | 11/2000 |
| JP | 2002-028126 | 1/2002 |
| JP | 2005-106878 | 4/2005 |
| JP | 2008-003108 | 1/2008 |
| JP | 2008-158198 | 7/2008 |

* cited by examiner

*Primary Examiner* — Alicia M Harrington
(74) *Attorney, Agent, or Firm* — Kenyon & Kenyon LLP

(57) ABSTRACT

The invention provides a high-performance objective lens that is capable of implementing focusing relative to an object point distance change with no or little angle-of-view change, and is well compatible with a high-pixel type imaging device. The objective optical system comprises, in order from an object side thereof, a first group of negative power, a second group of positive power, an aperture stop, and a third group of positive power. Only the second group moves thereby implementing focusing relative to an object point distance change, with satisfaction of the following conditions (1)-1, (1)-2 and (8):

$$\omega f > 60 \tag{1-1}$$

$$\omega n > 60 \tag{1-2}$$

$$-1.2 < f1/ff < -0.6 \tag{8}$$

where
$\omega f$ is a maximum half angle of view (°) upon viewing at a far distance object point,
$\omega n$ is a maximum half angle of view (°) upon close-up viewing,
$f1$ is a focal length of the first lens group, and
$ff$ is a focal length of the whole system upon viewing at a far distance. See FIG. 1.

1 Claim, 16 Drawing Sheets

Example 1

Example 1

Example 2

Example 3

Example 4

Example 5

Example 6

Example 7

Example 8

Example 1

Example 2

Example 3

Example 4

Example 5

Example 6

Example 7

Example 8

OBJECTIVE OPTICAL SYSTEM

CROSS REFERENCE TO RELATED APPLICATION

This application is a continuation of PCT International Application No. PCT/JP2010/002514 filed on Apr. 6, 2010, which claims priority to Japanese Patent Application No. 2009-099935, filed on Apr. 16, 2009, each of which is expressly incorporated herein in its entirety by reference thereto.

ART FIELD

The present invention relates generally to an objective optical system, and more particularly to an endoscopic objective optical system having focusing function and capable of close-up viewing as well as taking lenses used with other consumer-oriented compact cameras.

BACKGROUND OF THE INVENTION

Conventional objective lenses for general endoscopes have a viewing depth in a wide range of roughly 5 to 100 mm on the object side, although they have no focusing function. An endoscope with such an objective lens built in it primarily uses a CCD or other solid-state imaging device to provide images. In recent years, there has been mounting demand for making endoscopic image quality much higher so as to enhance diagnosis accuracy, and CCDs having much more pixels are now under development. The use of CCDs having much more pixels, however, leads to a need of bringing down the F-number of an associated objective lens so as to avoid image quality degradations due to diffraction. In addition, as CCD size grows large under the influence of an increasing number of pixels, it is also necessary to increase the focal length of the objective lens. For one thing and another, the viewing depth now becomes narrow. To make sure the viewing depth on a par with a conventional one, there is thus an increasing need for an objective lens having focusing function.

The primary purpose of such an endoscopic objective lens is that it can be used the same way as a general endoscopic objective lens: it is desired that there be no or little change of viewing with no or little angle-of-view change.

Patent Publication 1 discloses an objective lens having focusing function with limited angle-of-view fluctuations, which comprises two groups, negative and positive, or three groups, negative, positive and positive, wherein focusing is implemented by movement of the second group. Patent Publications 2 and 3 each disclose a two-group construction, positive and positive.

Besides, Patent Publications 4, 5 and 6 disclose an extended endoscopic objective lens capable of focusing on a near distance object point, which comprises three groups, positive, negative and positive, and in which focusing is implemented by movement of the second group. Patent Publication 7 shows an endoscopic objective lens of the type which comprises three groups, negative, positive and negative, and in which focusing is implemented by movement of the second group.

LISTING OF THE PRIOR ARTS

Listing of the Patent Publications

Patent Publication 1: JP(B) 55-15005
Patent Publication 2: JP(A) 2000-330015
Patent Publication 3: JP(A) 2002-28126
Patent Publication 4: JP(B) 61-44283
Patent Publication 5: JP(A) 6-317744
Patent Publication 6: JP(A) 11-316339
Patent Publication 7: JP(A) 2002-267002

SUMMARY OF THE INVENTION

According to one aspect of the invention, there is an objective optical system provided, which comprises, in order from an object side thereof, a first group of negative power, a second group of positive power, an aperture stop, and a third group of positive power, wherein:

only said second group moves thereby implementing focusing relative to an object point distance change, with satisfaction of the following conditions (1)-1, (1)-2 and (8):

$$\omega f > 60 \tag{1)-1}$$

$$\omega n > 60 \tag{1)-2}$$

$$-1.2 < f1/f\!f < -0.6 \tag{8}$$

where
$\omega f$ is a maximum half angle of view (°) upon viewing at a far distance object point,
$\omega n$ is a maximum half angle of view (°) upon close-up viewing,
f1 is a focal length of said first lens group, and
ff is a focal length of the whole system upon viewing at a far distance.

According to another aspect of the invention, there is an objective optical system provided, which comprises, in order from an object side thereof, a first group of negative power, a second group of positive power, an aperture stop, and a third group of positive power, wherein:

only said second group moves thereby implementing focusing relative to an object point distance change, with satisfaction of the following conditions (2) and (8):

$$0.8 < \omega n/\omega f < 1.2 \tag{2}$$

$$-1.2 < f1 < f\!f < -0.6 \tag{8}$$

where
$\omega t$ is a maximum half angle of view (°) upon viewing at a far distance object point,
$\omega n$ is a maximum half angle of view (°) upon close-up viewing,
f1 is a focal length of said first lens group, and
ff is a focal length of the whole system upon viewing at a far distance.

MODES FOR CARRYING OUT THE INVENTION

Figure 1A:
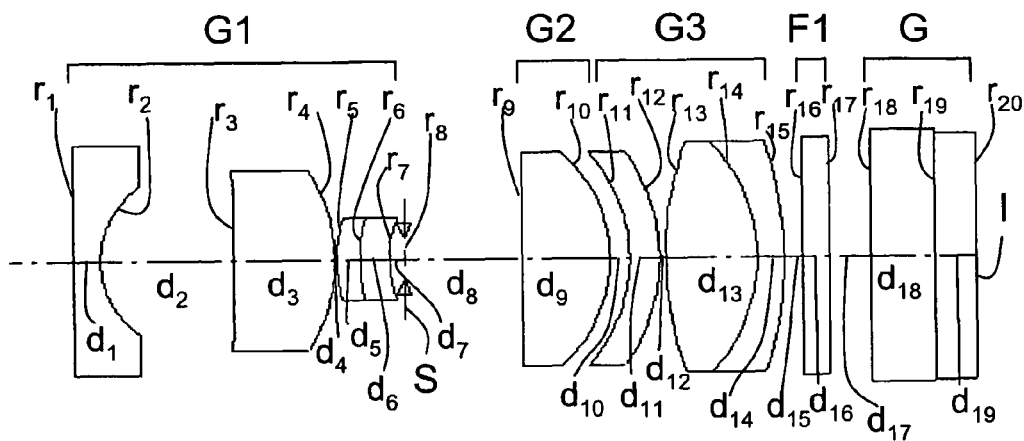
FIG. 1 is illustrative in section of the endoscopic objective optical system of Inventive Example 1 upon (a) ordinary viewing) and (b) close-up viewing.

Before explaining the examples of the inventive endoscopic objective optical system, some objective optical systems based on the invention will now be explained.

According to the first aspect of the invention, there is an objective optical system provided, which is characterized in that focusing can be implemented with respect to an object point distance change by movement of at least one lens group, with satisfaction of the following conditions (1)-1, (1)-2 and (2).

$$\omega f > 60 \tag{1}-1$$

$$\omega n > 60 \tag{1}-2$$

$$0.8 < \omega n/\omega f < 1.2 \tag{2}$$

where
$\omega f$ is the maximum half angle of view (°) upon viewing at a far distance object point, and
$\omega n$ is the maximum half angle of view (°) upon close-up viewing.

According to the second aspect of the invention, there is an objective optical system provided, which is characterized by comprising at least three groups, wherein at least one lens group moves thereby implementing focusing with respect to an object point distance change, with satisfaction of the following conditions (1)-1 and (1)-2.

$$\omega f > 60 \tag{1}-1$$

$$\omega n > 60 \tag{1}-2$$

where
$\omega f$ is the maximum half angle of view (°) upon viewing at a far distance object point, and
$\omega n$ is the maximum half angle of view (°) upon close-up viewing.

According to the third aspect of the invention, there is an objective optical system provided, which is characterized by comprising at least three groups, wherein at least one lens group moves thereby implementing focusing with respect to an object point distance change, with satisfaction of the following condition (2).

$$0.8 < \omega n/\omega f < 1.2 \tag{2}$$

where
$\omega f$ is the maximum half angle of view (°) upon viewing at a far distance object point, and
$\omega n$ is the maximum half angle of view (°) upon close-up viewing.

For focusing in association with an object point fluctuation from ordinary endoscopic viewing at a far distance object point to close-up viewing at a near distance object point, it is required to implement focusing by movement of at least one group. Focusing may be implemented by movement of any of the groups that form part of the objective optical system, and that moving group may be defined by one or more groups. However, when the moving group is defined by one single group, there is a merit of simplifying the mechanical structure involved.

Focusing may also be implemented by movement of the whole optical system or an imaging device itself; however, that is not preferable because the moving group(s) or the imaging device increases in weight, there is a growing load on the driving mechanism involved, and the mechanism itself must be made bulky.

To reduce the risk of overlooking affected sites during in-vivo screening, the objective optical system should desirously be set up as an arrangement as wide-angle as possible; the angle of field must be at least 120° all over the object point area. For this reason, the half angle of view that is a field range should desirously satisfy at least the following conditions in terms of wide-angle field.

$$\omega f > 60 \tag{1}-1$$

$$\omega n > 60 \tag{1}-2$$

Further, it is desired that during focusing, angle-of-view changes be reduced as much as possible. Amounts of angle-of-view changes exceeding 20% are not preferable because angle-of-field changes become noticeable during focusing, and object images look as if electronically enlarged. Accordingly, the ratio of the viewing angle upon focusing should desirously satisfy the following condition (2).

$$0.8 < \omega n/\omega f < 1.2 \tag{2}$$

Upon focusing with the position of an object changing from a far distance object point to a near distance object point, it is not preferable for the lower limit to Condition (2) to be short of 0.8, because focus is on a blurred image while, at the same time, object images look as if enlarged. It is again not preferable for the upper limit to Condition (2) to exceed 1.2, because this time the object images look as if scaled down. If the angle-of-view changes come within the range of Condition (2), it is then possible to implement reasonable focusing because the operator is less susceptible of large changes in the viewing range.

More desirously, Condition (2) should be narrowed down to:

$$0.9 < \omega n/\omega f < 1.1 \tag{2}$$

In the range of Condition (2), the amount of angle-of-view changes is limited to less than 10% so that the effect brought about by Condition (2) grows much stronger.

To achieve further reductions of the angle-of-view changes, it is desired to satisfy the following condition (3).

$$0.85 < fn/ff < 1.15 \tag{3}$$

where
fn is the focal length of the whole system upon viewing at a near distance, and
ff is the focal length of the whole system upon viewing at a far distance.

If the range of Condition (3) is abided by, it is then possible to limit angle-of-view changes upon focusing to within the range of Condition (2). Exceeding the upper limit of 1.15 to Condition (3) or being short of the lower limit of 0.85 is not preferable because the angle-of-view changes grow large. Being short of the lower limit to Condition (3) is again not preferable because the depth of focus upon viewing at a far distance becomes shallow, rendering the ease-of-use of the optical system worse during viewing such as screening. The closer to the object point, the shallower the depth of viewing becomes; however, exceeding the upper limit to Condition (2) is not preferable because the depth of field becomes too shallow upon viewing at a near distance.

More desirously, Condition (3) should be narrowed down:

$$0.9 < fn/f\!f < 1.1 \quad (3)$$

Within the range of Condition (3), the effect of Condition (3) would become much stronger.

The angle-of-view changes occur not only through focal length fluctuations but also via distortion changes. For this reason, it is desired to satisfy the following Condition (9):

$$0.8 < DTLn \times f\!f/DTLf \times fn < 1.2 \quad (9)$$

where

DTLn is distortion at the maximum image height upon viewing at a near distance, and DTLf is distortion at the maximum image height upon viewing at a far distance.

Being short of the lower limit of 0.8 to Condition (9) is not preferable because the field range becomes narrow upon focusing from a far distance object point to a near distance object point, and exceeding the upper limit of 1.2 to Condition (9) is again not preferable because the field range becomes wide upon focusing.

Given the inventive objective optical system comprising two or more groups, there may be a focusing mechanism achieved; with only two groups, however, there is a tendency for image plane fluctuations to grow large upon focusing. This may not matter where the object point range capable of focusing remains narrow. Still it is desired to have three or more groups if the fact that focusing is usually implemented in a certain wide object point range is taken into account.

Preferably, the moving lens group should be the second group as counted from the object side. If the moving group is the first group, a fixed cover glass must then be located in front of the first group and in a position flush with the end of the endoscope. As the first group moves toward the image side, it will cause light rays at that cover glass to go high, giving rise to an increased diameter.

The moving group should also be a positive group for the purpose of preventing the angle of view from fluctuating upon focusing. Defining the moving group by a negative group is not preferable because there are entrance pupil position fluctuations to which large angle-of-view changes are incidental.

If the inventive objective optical system comprises three groups, it is then possible to achieve an optical system of performance high enough to be compatible with a high-pixel type imaging device. As long as the moving or second group is defined by a positive lens group in such a way as to reduce image plane fluctuations during focusing, the first, and the third group may be either of positive power or of negative power.

Although the lens in the second group may be constructed of the positive lens having any desired shape, it is more desirous that the positive lens be a positive meniscus lens convex on its object side. Especially when the first group is of negative power and the third group is of positive power, this can be optimum for holding back image plane fluctuations during focusing.

When the first group comprises a plurality of lenses, it is desired that the first group comprise, at least in order from the object side, a first lens of negative power and a second lens of positive power. Especially in a lens arrangement where the third group is a positive one, it is required for the first group to have a lens of strong negative power because the three groups are all of positive power. For this reason, it is desired that the negative power of the first lens be stronger than the positive power of the second lens, as in Condition (11).

$$|f11/f12| < 0.8 \quad (11)$$

where f11 is the focal length of the first lens, and f12 is the focal length of the second lens.

As Condition (11): |f11/f12| exceeds 0.8, it causes the negative power in the first group to become relatively weak, rendering it difficult to make sure any wide-angle arrangement.

When the first group is a negative one, it is desired to satisfy the following condition (6):

$$-0.6 < f1/f2 < -0.1 \quad (6)$$

where f1 is the focal length of the first group, and f2 is the focal length of the second group.

As the lower limit of −0.6 to Condition (6) is not reached, it causes light rays to grow high at the first lens, resulting in an increased lens diameter. As the upper limit of −0.1 to Condition (6) is exceeded, it causes the power of the second group to become relatively weak, resulting in some considerable field curvature and coma and, hence, incurring image quality degradation at the periphery.

It is further desired for the focal length of the first group to satisfy the following condition (8):

$$-1.2 < f1/f\!f < -0.6 \quad (8)$$

where f1 is the focal length of the first group, and ff is the focal length of the whole system upon viewing at a far distance.

As the lower limit of −1.2 to Condition (8) is not reached, it causes the power of the first group to become weak and the amount of distortion occurring at the first surface to become small, with the result that the angle of view becomes small, rendering satisfaction of Condition (1) difficult. As the upper limit of −0.6 to Condition (8) is exceeded, it causes the first group to be more sensitive to angle-of-view errors. For such a wide-angle optical system as intended herein, this is not preferable because of being responsible for shading in fabrication processes.

Referring to the lens arrangement of the first group, the first lens of negative power that remains fixed during focusing and is concave on its image side is located on the most object side. This first lens may be either a plano-concave lens or a concave meniscus lens. The first lens is positioned at the tip of an endoscope; the plano-concave lens would have a merit of being hardly flawed, because there is no prominence on the lens surfaces. The concave meniscus lens would be preferable for a wide-angle arrangement, making it easy to achieve a wide-field objective lens in particular with a ωf greater than 70°.

With the third group of positive power, it is possible to make the whole length of the optical system short while making sure the back focus. To make sure performance in relation to the second group, it is preferable to satisfy the following condition (4):

$$0.3 < f2/f3 < 6 \quad (4)$$

where f2 is the focal length of the second group, and f3 is the focal length of the third group.

Being short of the lower limit of 0.3 to Condition (4) is not preferable, because it causes the power of the second group to grow too strong, resulting in an under field tilt, and because it gives rise to larger image plane fluctuations due to focusing. Exceeding the upper limit of 6 to Condition (4) is again not preferable. This is because the power of the second group becomes weak and the sensitivity of the image plane to focusing become low; there is a need of moving the lens more than required. It is to be understood that the amount of movement of the lens must be reduced as much as possible for the purpose of easing off loads on the mechanical parts of the drive mechanism or the like.

More desirously, Condition (4) should be narrowed down:

$$0.6 < f2/f3 < 4 \tag{4}'$$

If the lower limit of 0.6 to Condition (4) is abided by, then correction of field curvature is facilitated, and if the upper limit of 4 to Condition (4) is abided by, then it provides the optimum amount of movement of the lens at which the drive system such as an actuator works properly.

Referring the lens arrangement of the third group, it should preferably be made up of, in order from its object side, a double-convex lens and a cemented lens in which a positive lens and a negative lens are cemented together. More specifically, the double-convex lens is located for the purpose of keeping light rays from going high at the third group, and the cemented lens is located for the purpose of correcting longitudinal chromatic aberration and chromatic aberration of magnification in a well-balanced state.

However, it is to be understood that the third group is not necessarily limited to that arrangement; for instance, there is a possible arrangement made up of a cemented lens in which three lenses: negative, positive and negative lenses are cemented together. In this case, ray height has been well lowered at the second group; the main purpose of the third group is to make correction of chromatic aberrations.

When the third group is set up as a negative group, it is desired to satisfy the following condition (5):

$$-0.25 < f2/f3 < 0 \tag{5}$$

where f2 is the focal length of the second group, and f3 is the focal length of the third group.

As the power of the third group becomes weak, the back focus becomes short. Focus adjustment is implemented between the final lens and the imaging device. As the lower limit of −0.25 to Condition (5) is not reached, it causes the power of the third group to become too weak, rendering it difficult to make sure that spacing. As the upper limit of 0 to Condition (5) is exceeded, it renders correction of chromatic aberration of magnification difficult, giving rise to a lowering of resolution at the periphery of the screen.

Although depending on the lens type applied, it is desired to satisfy the following Condition (7):

$$-0.24 < f3/f1 < -1.5 \tag{7}$$

where f1 is the focal length of the first group, and f3 is the focal length of the third group.

Condition (7) is provided to reduce field curvature and minimize image plane fluctuations during focusing. As the lower limit of −2.4 to Condition (7) is not reached, it causes the power of the first group to become weaker relative to that of the third group, tending to end up with an over field tilt. Exceeding the upper limit of −1.5 to Condition (7) is not preferable because the power of the first group grows too large, ending up with an under field tilt. For this reason, deviations from the range of Condition (7) incur image quality degradation: an image that is in focus at the center but out of focus at the periphery.

As regards the amount of movement of the moving or second group, it is desired to satisfy the following Condition (10):

$$0.07 < \Delta d/ff < 0.38 \tag{10}$$

where

Δd is the amount of movement of the lens in the moving group upon focusing from a far distance object point to a near distance object point, and ff is the focal length of the whole system upon viewing at a far distance.

As the lower limit of 0.07 to Condition (10) is not reached, it causes the amount of movement to become too small: it causes the amount of movement to become small relative to changes in a constant object point distance, rendering the image plane position more sensitive to lens stop accuracy errors. Especially at a near distance object point having a shallow focal depth, out-of-focus is likely. Exceeding the upper limit of 0.38 to Condition (10) is contradictory to size reductions because increases in the amount of movement lead to an increase in the whole length of the lens system.

In the inventive objective optical system, there is an aperture stop located before or after the second group. Irrespective of whether the aperture stop is movable together with the moving group or remains fixed with the first or the third group, pupil position fluctuations remain more reduced, so do angle-of-view changes and F-number fluctuations during focusing.

However, this aperture stop works more effectively as it is positioned in front of the third group and remains fixed during focusing. With the aperture stop remaining fixed during focusing, the exit pupil position could remain invariable so that the angle of incidence of light rays on the imaging device could be kept constant. Thus, the optical system is not affected by shading even upon focusing.

If the aperture stop is located at the aforesaid position, then it is also possible to reduce F-number fluctuations more so that wherever there is an object point, it is possible to keep some depth of field.

Some embodiments of the inventive endoscopic objective optical system are now explained with reference to the following examples.

Example 1

Figure 1B:
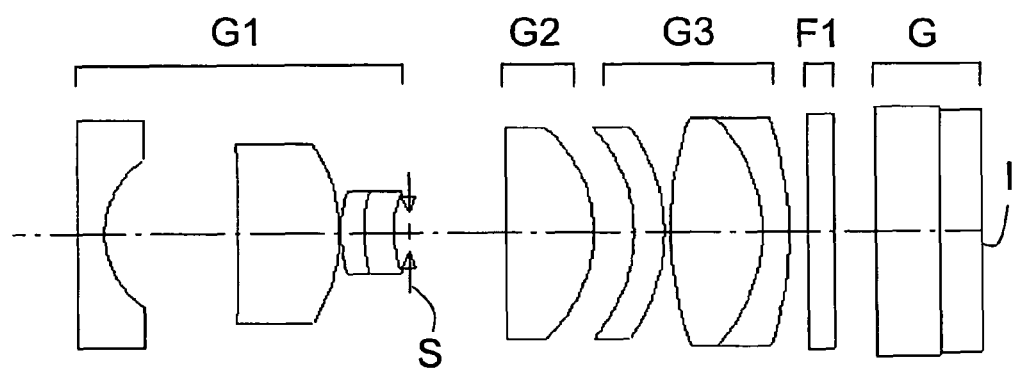

FIG. 1 is a sectional view, as taken through the optical axis, of the construction or arrangement of the endoscopic objective optical system exemplified as Example 1. Lens data on Example 1 will be given later in Table 1. The values of variation parameters in two states: (a) ordinary viewing and (b) close-up viewing will be set out in Table 2. In the numeral data given later, the surface numbers of optical surfaces as counted from the object side are indicated by "No", with the radius of curvature indicated by "r", the surface-to-surface spacing or air spacing by "d", the e-line refractive index by "ne", and the Abbe constant by "vd". The radius of curvature, and the surface-to-surface spacing is given in mm. Referring here to FIG. 1, optical surfaces having surface "Nos. 1, 2, 3, . . . " are indicated by $r_1, r_2, r_3, \ldots$, and the surface-to-surface spacing or air spacing between surface Nos. 1 and 2, Nos. 2 and 3, Nos. 3 and 4, . . . are indicated by $d_1, d_2, d_3, \ldots$.

The optical system shown in FIG. 1 is in two states: (a) ordinary viewing and (b) close-up viewing. The endoscopic objective optical system here is built up of, in order from the object side, the first group G1 of positive refracting power, the second group G2 of positive refracting power, and the third group G3 of positive refracting power. The first group G1 is made up of, in order from the object side, a plano-concave negative lens, a positive meniscus lens concave on its object side and a negative cemented lens in which a positive meniscus convex on its object side and a negative meniscus lens convex on its object side are cemented together. The second group G2 is made up of one plano-convex positive lens, and moves on the optical axis to implement focusing. The aperture stop S is located between the first group G1 and the second group G2, and remains fixed in the rear of the first group G1 during focusing. The third group G3 is made up of, in order from the object side, a negative meniscus lens concave on its object side and a positive cemented lens in which a double-convex positive lens and a negative meniscus lens convex on its image plane side are cemented together. In the rear of the third group G3, there is the plane-parallel plate F1 located that is a filter for cutting off light having a specific wavelength, for instance, 1,060 nm YAG laser, 810 nm semiconductor laser or light in the near infrared region. An imaging device located near the image plane I of the endoscopic objective optical system is combined with the aforesaid endoscopic objective optical system, providing an imaging optical system. The imaging device has the cover glass G cemented to it for protection of the imaging plane.

Further, the aforesaid high-pixel type imaging device is used as the imaging device so that high-definition images are obtained at the respective object points.

Figure 9A:
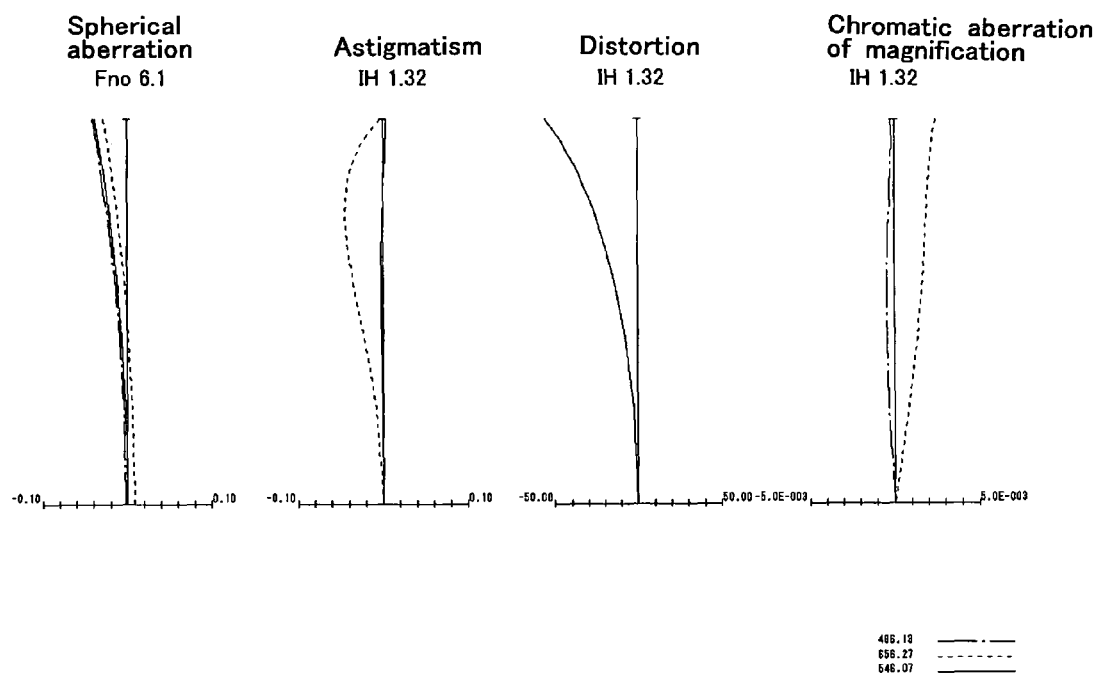
FIG. 9 is aberration curve diagrams for Example 1 upon (a) ordinary viewing and (b) close-up viewing.
Figure 9B:
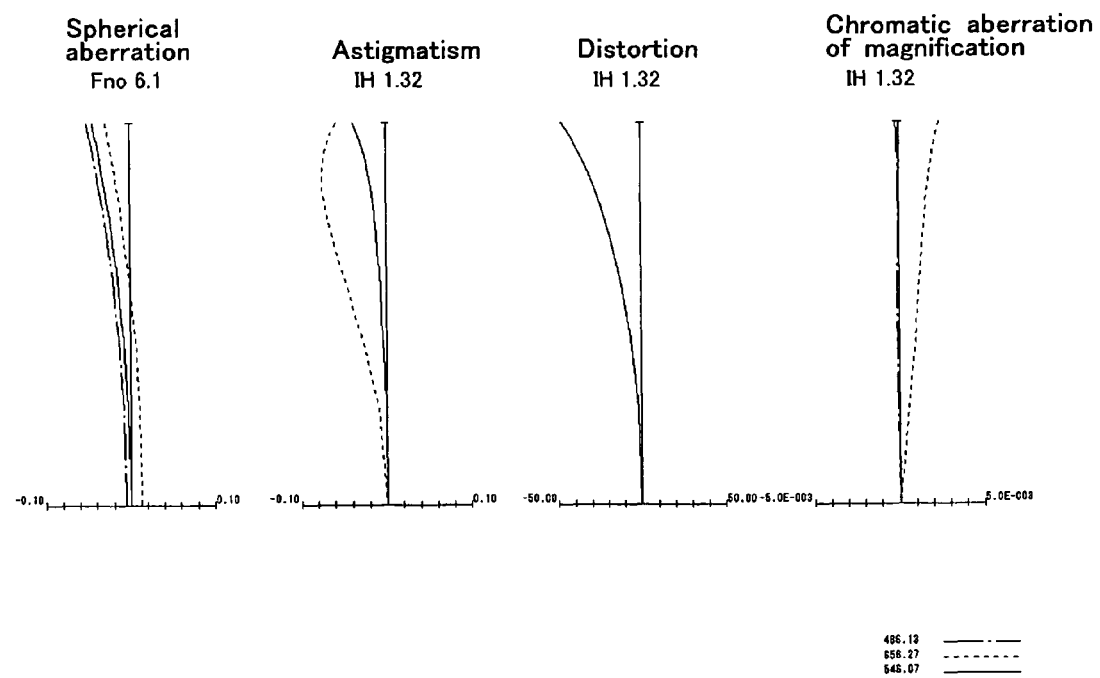

The inventive imaging optical system set up as described above satisfies all Conditions (1) to (11) but (5) to (8). The focal lengths of the first G1, the second G2 and the third group G3 are set at proper values so that the imaging optical system can be made compact without image quality degradation. FIGS. 9(a) and 9(b) are aberration curve diagrams upon (a) ordinary viewing and (b) close-up viewing, respectively. Fno is the F-number, and IH is the maximum image height (mm). The solid and broken lines in the astigmatism diagram stand for the sagittal and meridional image planes, respectively. Besides distortion, the abscissa stands for the amount of aberrations (mm), provided that5 "E-003" means "$\times 10^{-3}$". The abscissa for distortion stands for the amount of aberrations (%), and the wavelength (legend) of the aberration curves is given in nm. The same shall apply hereafter.

Example 2

Figure 2A:
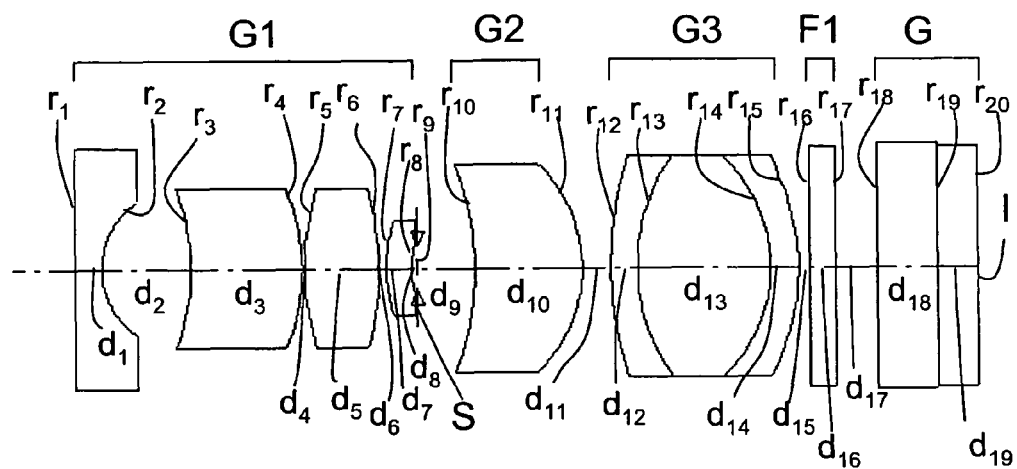
FIG. 2 is illustrative, as in FIG. 1, of the endoscopic objective optical system of Inventive Example 2.
Figure 2B:
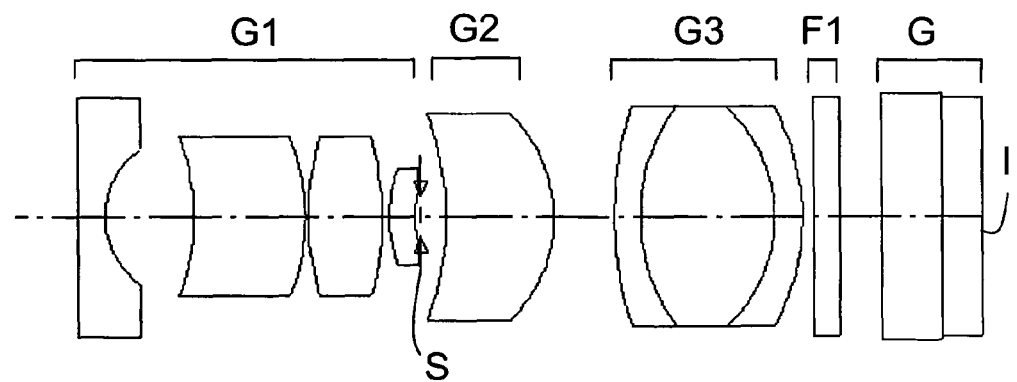

FIG. 2 is a sectional view, as taken through the optical axis, of the construction or arrangement of the endoscopic objective optical system exemplified as Example 2. Lens data on Example 2 will be given later in Table 3. The values of variation parameters in two states: (a) ordinary viewing and (b) close-up viewing will be set out in Table 4.

The optical system shown in FIG. 2 is in two states: (a) ordinary viewing and (b) close-up viewing. The endoscopic objective optical system here is built up of, in order from the object side, the first group G1 of positive refracting power, the second group G2 of positive refracting power, and the third group G3 of positive refracting power. The first group G1 is made up of, in order from the object side, a plano-concave negative lens, a positive meniscus lens concave on its object side, a double-convex positive lens and a negative meniscus lens convex on its object side. The second group G2 is made up of one positive meniscus lens concave on its object side, and moves on the optical axis to implement focusing. The aperture stop S is located between the first group G1 and the second group G2, and remains fixed in the rear of the first group G1 during focusing. The third group G3 is made up of a positive cemented triplet in which a negative meniscus lens convex on its object side, a double-convex positive lens and a negative meniscus lens concave on its objet side are cemented together in order from the object side. In the rear of the third group G3, there is the plane-parallel plate F1 located that is a filter for cutting off light having a specific wavelength, for instance, 1,060 nm YAG laser, 810 nm semiconductor laser or light in the near infrared region. An imaging device located near the image plane I of the endoscopic objective optical system is combined with the aforesaid endoscopic objective optical system, providing an imaging optical system. The imaging device has the cover glass G cemented to it for protection of the imaging plane.

Further, the aforesaid high-pixel type imaging device is used as the imaging device so that high-definition images are obtained at the respective object points.

Figure 10A:
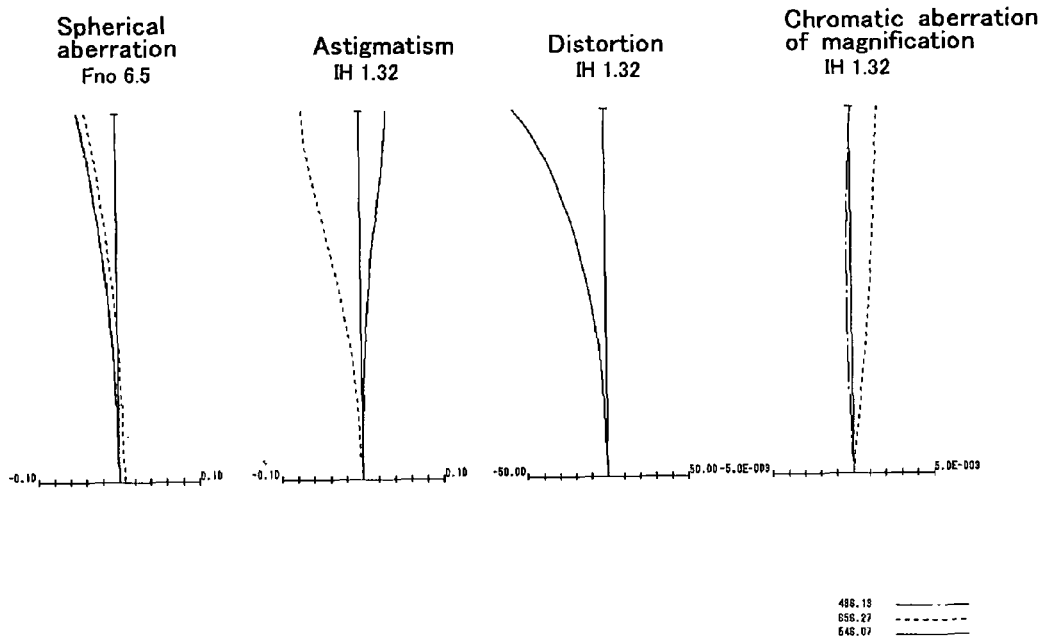
FIG. 10 is aberration curve diagrams for Example 2 upon (a) ordinary viewing and (b) close-up viewing.
Figure 10B:
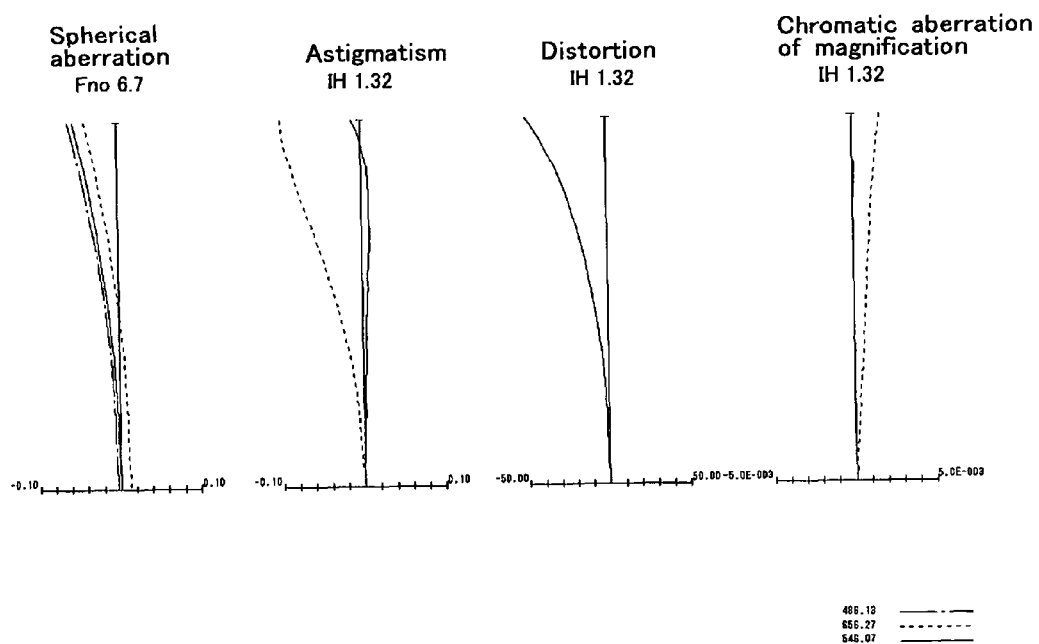

The inventive imaging optical system set up as described above satisfies all Conditions (1) to (11) but (5) to (8). The focal lengths of the first G1, the second G2 and the third group G3 are set at proper values so that the imaging optical system can be made compact without image quality degradation. FIGS. 10(a) and 10(b) are aberration curve diagrams upon (a) ordinary viewing and (b) close-up viewing, respectively.

Example 3

Figure 3A:
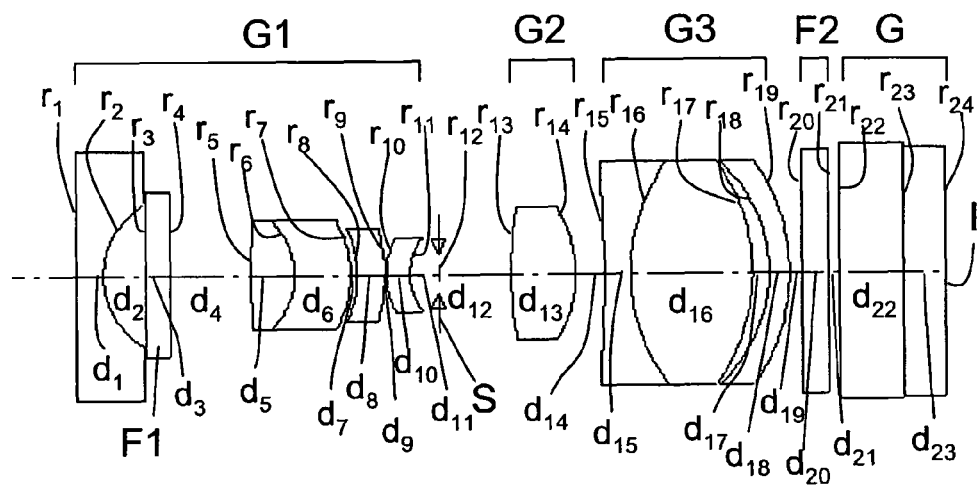
FIG. 3 is illustrative, as in FIG. 1, of the endoscopic objective optical system of Inventive Example 3.
Figure 3B:
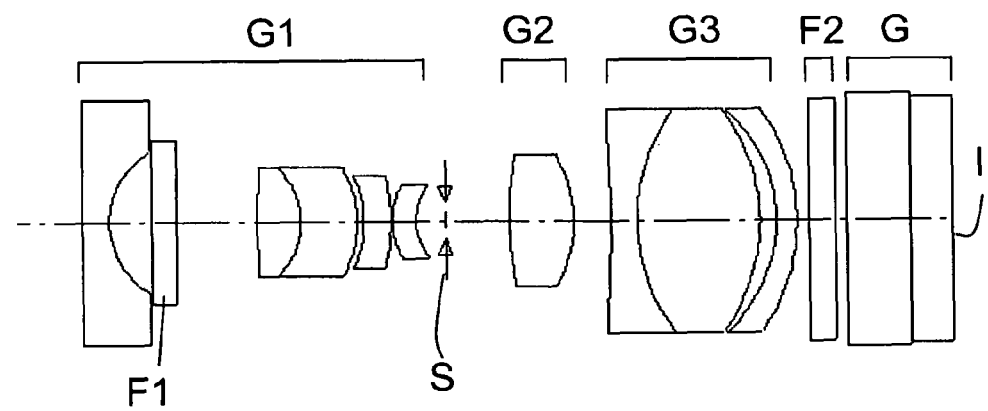

FIG. 3 is a sectional view, as taken through the optical axis, of the construction or arrangement of the endoscopic objective optical system exemplified as Example 3. Lens data on Example 3 will be given later in Table 5. The values of variation parameters in two states: (a) ordinary viewing and (b) close-up viewing will be set out in Table 6.

Figure 6A:
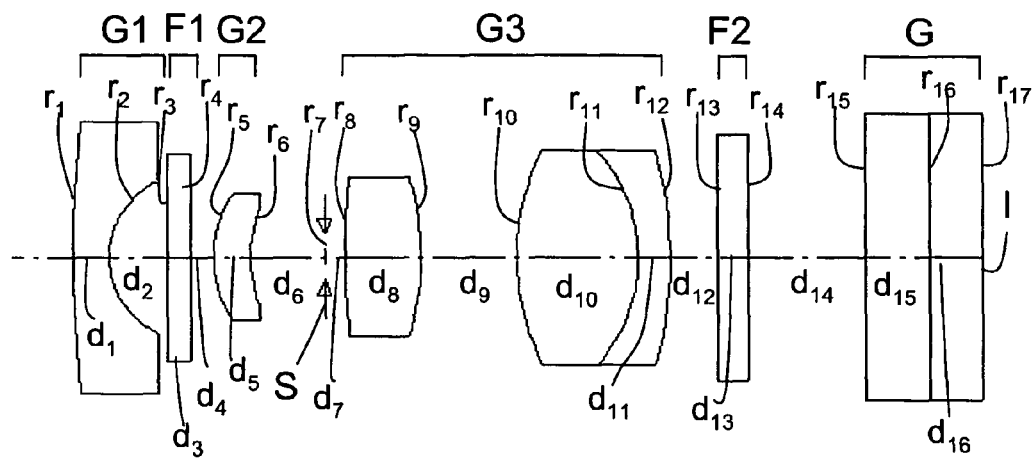
FIG. 6 is illustrative, as in FIG. 1, of the endoscopic objective optical system of Inventive Example 6.
Figure 6B:
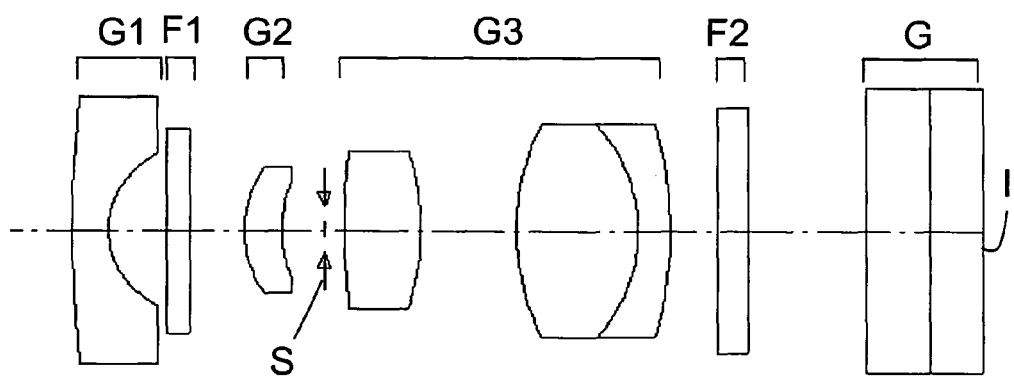

The optical system shown in FIG. 6 is in two states: (a) ordinary viewing and (b) close-up viewing. The endoscopic objective optical system here is built up of, in order from the object side, the first group G1 of positive refracting power, the second group G2 of positive refracting power, and the third group G3 of negative refracting power. The first group G1 is made up of, in order from the object side, a plano-concave negative lens, a positive cemented lens in which a double-convex positive lens and a negative meniscus lens concave on its object side are cemented together, a negative meniscus lens concave on its object side, and a negative meniscus lens convex on its object side. The second group G2 is made up of one double-convex positive lens, and moves on the optical axis to implement focusing. The aperture stop S is located between the first group G1 and the second group G2, and remains fixed in the rear of the first group G1 during focusing. The third group G3 is made up of, in order from the object side, a positive cemented lens in which a double-concave negative lens and a double-convex positive lens are cemented together, and a negative meniscus lens convex on its image plane side. In the rear of the plano-concave negative lens in the first group G1, and in the rear of the third group G3, there are the plane-parallel plates F1 and F2 located, each a filter for cutting off light having a specific wavelength, for instance, 1,060 nm YAG laser, 810 nm semiconductor laser or light in the near infrared region. An imaging device located near the image plane I of the endoscopic objective optical system is combined with the aforesaid endoscopic objective optical system, providing an imaging optical system. The imaging device has the cover glass G cemented to it for protection of the imaging plane.

Further, the aforesaid high-pixel type imaging device is used as the imaging device so that high-definition images are obtained at the respective object points.

Figure 11A:
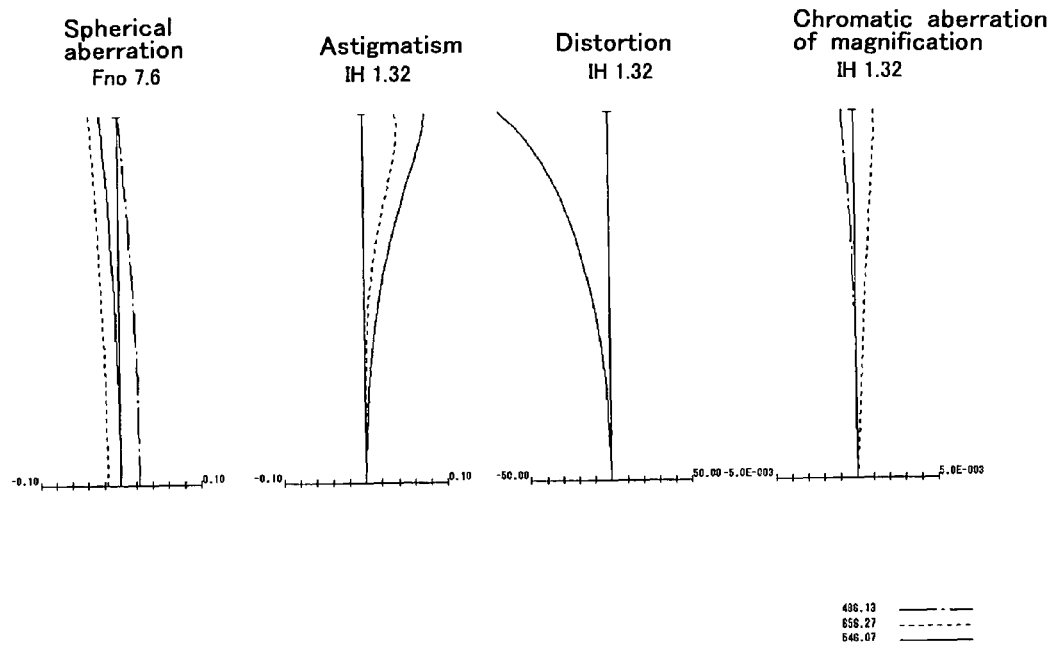
FIG. 11 is aberration curve diagrams for Example 3 upon ordinary viewing (a) and (b) close-up viewing.
Figure 11B:
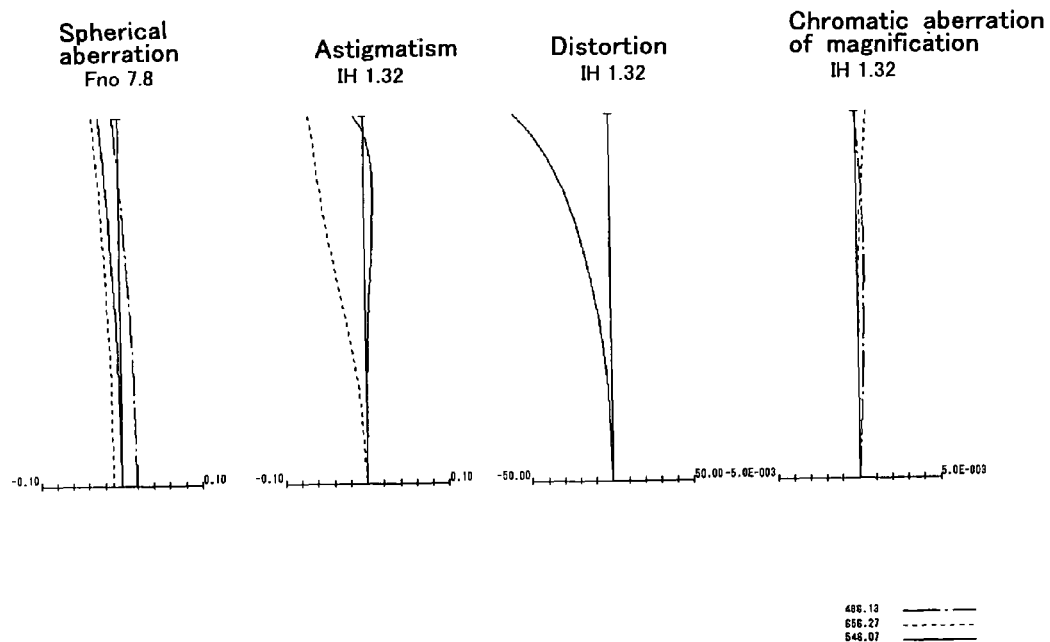

The inventive imaging optical system set up as described above satisfies all Conditions (1) to (11) but (4) and (6) to (8). The focal lengths of the first G1, the second G2 and the third group G3 are set at proper values so that the imaging optical system can be made compact without image quality degradation. FIGS. 11(a) and 11(b) are aberration curve diagrams upon (a) ordinary viewing and (b) close-up viewing, respectively.

Example 4

Figure 4A:
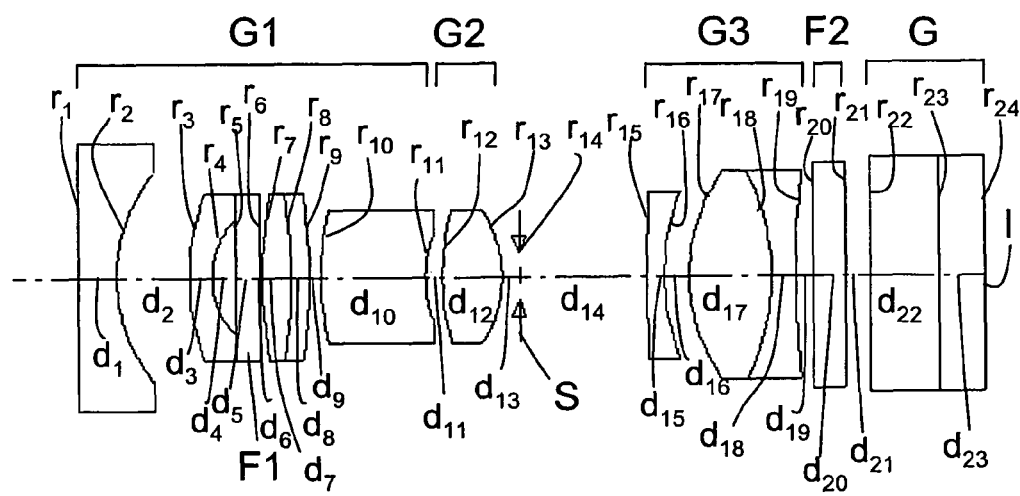
FIG. 4 is illustrative, as in FIG. 1, of the endoscopic objective optical system of Inventive Example 4.
Figure 4B:
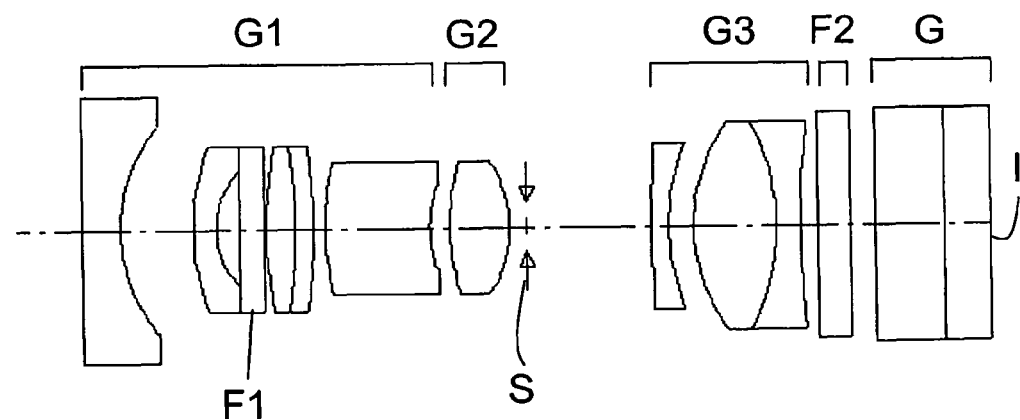

FIG. 4 is a sectional view, as taken through the optical axis, of the construction or arrangement of the endoscopic objective optical system exemplified as Example 4. Lens data on Example 4 will be given later in Table 7. The values of variation parameters in two states: (a) ordinary viewing and (b) close-up viewing will be set out in Table 8.

The optical system shown in FIG. 4 is in two states: (a) ordinary viewing and (b) close-up viewing. The endoscopic objective optical system here is built up of, in order from the object side, the first group G1 of negative refracting power, the second group G2 of positive refracting power, and the third group G3 of negative refracting power. The first group G1 is made up of, in order from the object side, a plano-concave negative lens, a positive meniscus lens concave on its object side, a positive cemented lens in which a double-convex positive lens and a negative meniscus lens convex on its object side are cemented together, and a negative meniscus lens convex on its object side. The second group G2 is made up of one double-convex positive lens, and moves on the optical axis to implement focusing. The third group G3 is made up of, in order from the object side, a negative meniscus lens convex on its image plane side and a positive cemented lens in which a double-convex positive lens and a double-concave negative lens are cemented together. The aperture stop S is located between the first group G1 and the second group G2, and moves together with the second group G2 during focusing. In the rear of the third group G3, there are the plane-parallel plates F1 and F2 located, each a filter for cutting off light having a specific wavelength, for instance, 1,060 nm YAG laser, 810 nm semiconductor laser or light in the near infrared region. An imaging device located near the image plane I of the endoscopic objective optical system is combined with the aforesaid endoscopic objective optical system, providing an imaging optical system. The imaging device has the cover glass G cemented to it for protection of the imaging plane.

Further, the aforesaid high-pixel type imaging device is used as the imaging device so that high-definition images are obtained at the respective object points.

Figure 12A:
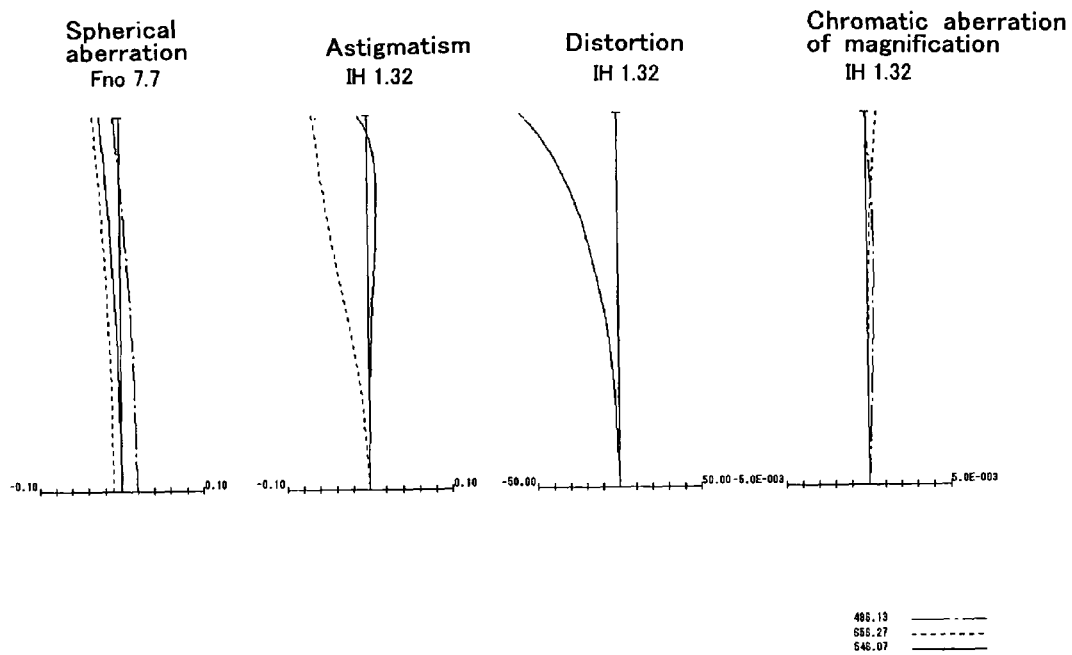
FIG. 12 is aberration curve diagrams for Example 4 upon (a) ordinary viewing and (b) close-up viewing.
Figure 12B:
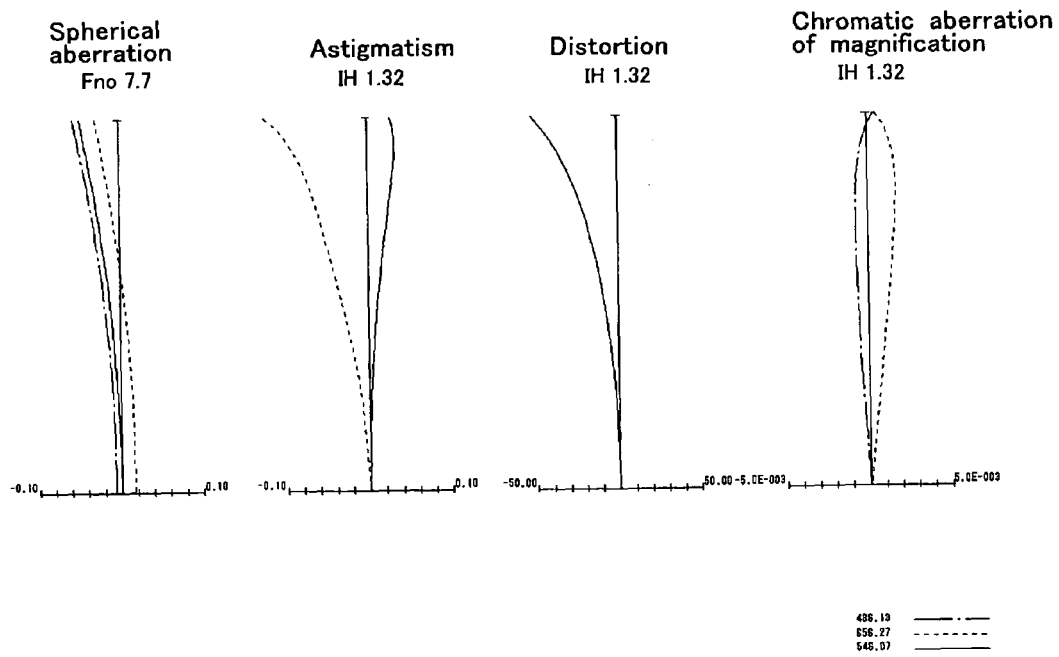

The inventive imaging optical system set up as described above satisfies all Conditions (1) to (11) but (4), (7), (8), (10) and (11). The focal lengths of the first G1, the second G2 and the third group G3 are set at proper values so that the imaging optical system can be made compact without image quality degradation. FIGS. 12(a) and 12(b) are aberration curve diagrams upon (a) ordinary viewing and (b) close-up viewing, respectively.

Example 5

Figure 5A:
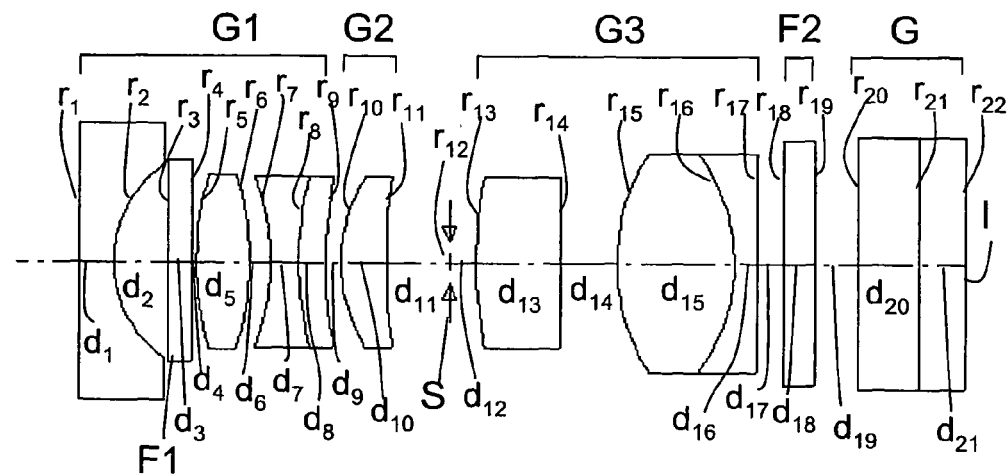
FIG. 5 is illustrative, as in FIG. 1, of the endoscopic objective optical system of Inventive Example 5.
Figure 5B:
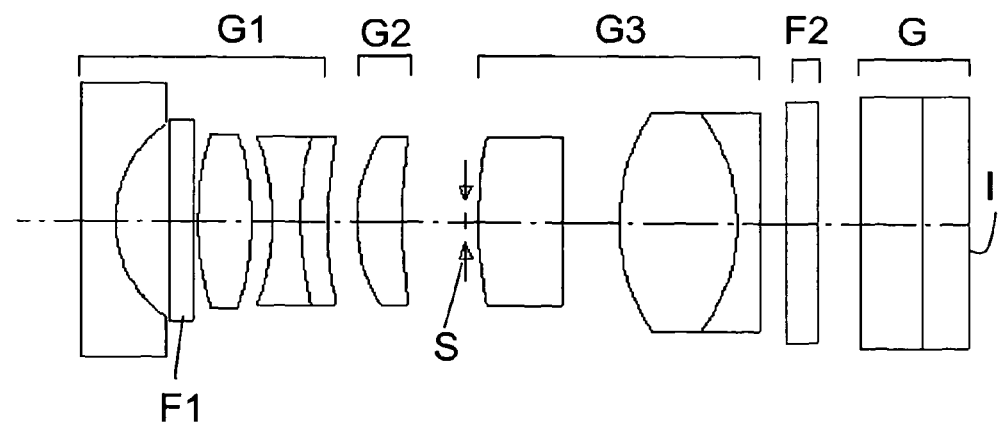

FIG. 5 is a sectional view, as taken through the optical axis, of the construction or arrangement of the endoscopic objective optical system exemplified as Example 5. Lens data on Example 5 will be given later in Table 9. The values of variation parameters in two states: (a) ordinary viewing and (b) close-up viewing will be set out in Table 10.

The optical system shown in FIG. 5 is in two states: (a) ordinary viewing and (b) close-up viewing. The endoscopic objective optical system here is built up of, in order from the object side, the first group G1 of negative refracting power, the second group G2 of positive refracting power, and the third group G3 of positive refracting power. The first group G1 is made up of, in order from the object side, a plano-concave negative lens, a double-convex positive lens and a negative cemented lens in which a double-concave negative lens and a positive meniscus lens convex on its object side are cemented together. The second group G2 is made up of one positive meniscus lens convex on its object side, and moves on the optical axis to implement focusing. The third group G3 is made up of, in order from object side, a positive meniscus lens convex on its object side and a positive cemented lens in which a double-convex positive lens and a double-concave negative lens are cemented together. The aperture stop S is located between the second group G2 and the third group G3, and moves together with the second group G2 during focusing. In the rear of the plano-concave negative lens in the first group G1, and the in the rear of the third group G3, there are the plane-parallel plates F1 and F2, each a filter for cutting off light having a specific wavelength, for instance, 1,060 nm YAG laser, 810 nm semiconductor laser or light in the near infrared region. An imaging device located near the image plane I of the endoscopic objective optical system is combined with the aforesaid endoscopic objective optical system, providing an imaging optical system. The imaging device has the cover glass G cemented to it for protection of the imaging plane.

Further, the aforesaid high-pixel type imaging device is used as the imaging device so that high-definition images are obtained at the respective object points.

Figure 13A:
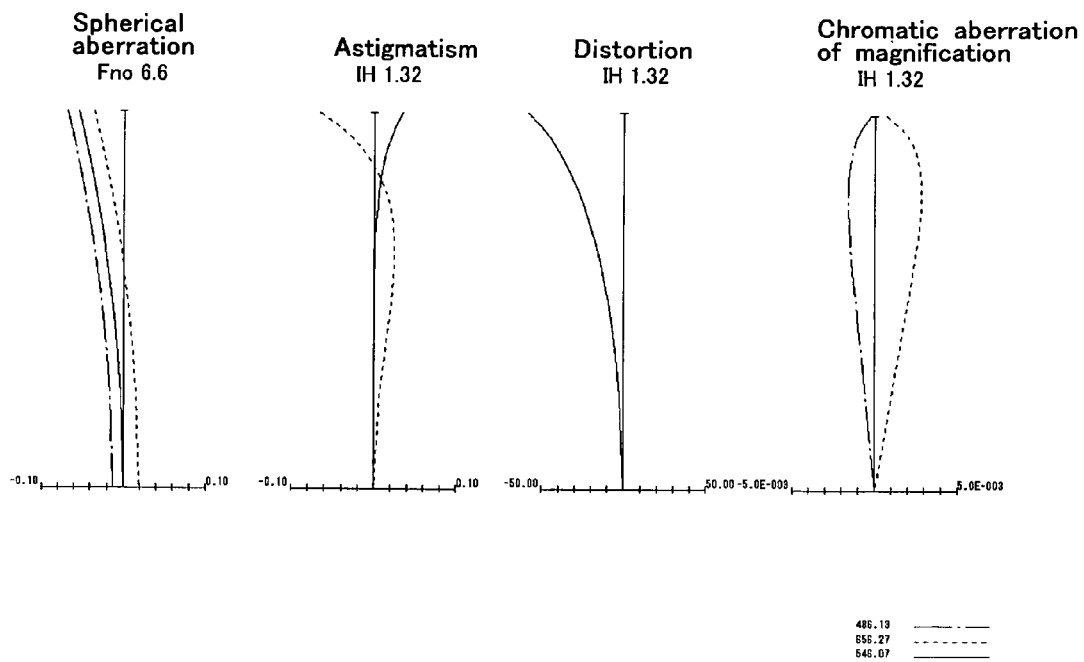
FIG. 13 is aberration curve diagrams for Example 5 upon (a) ordinary viewing and (b) close-up viewing.
Figure 13B:
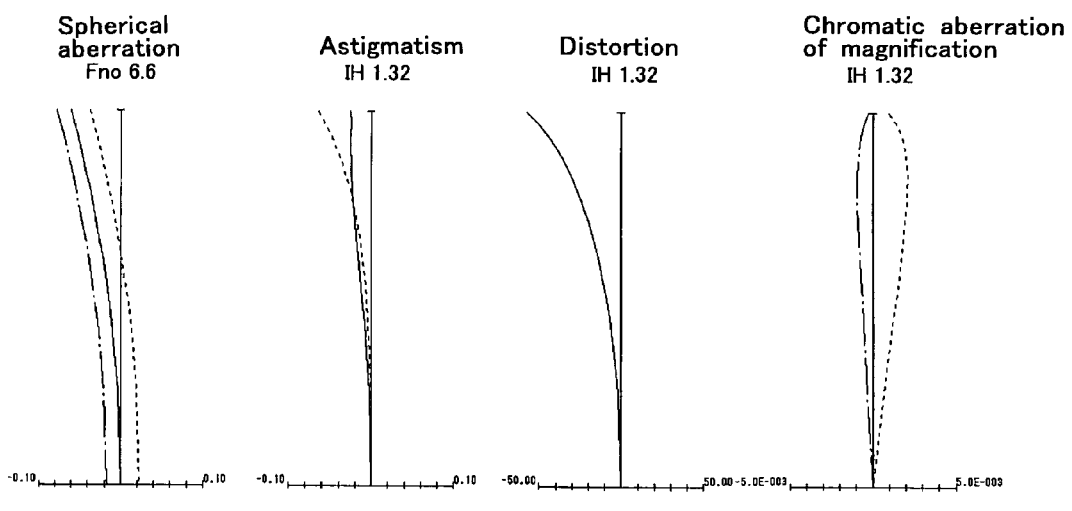

The inventive imaging optical system set up as described above satisfies all Conditions (1) to (11) but (5). The focal lengths of the first G1, the second G2 and the third group G3 are set at proper values so that the imaging optical system can be made compact without image quality degradation. FIGS. 13(a) and 13(b) are aberration curve diagrams upon (a) ordinary viewing and (b) close-up viewing, respectively.

Example 6

FIG. 6 is a sectional view, as taken through the optical axis, of the construction or arrangement of the endoscopic objective optical system exemplified as Example 6. Lens data on Example 6 will be given later in Table 11. The values of variation parameters in two states: (a) ordinary viewing and (b) close-up viewing will be set out in Table 12.

The optical system shown in FIG. 6 is in two states: (a) ordinary viewing and (b) close-up viewing. The endoscopic objective optical system here is built up of, in order from the object side, the first group G1 of negative refracting power, the second group G2 of positive refracting power, and the third group G3 of positive refracting power. The first group G1 is made up of one negative meniscus lens convex on its object side. The second group G2 is made up of one positive meniscus lens convex on its object side, and moves on the optical axis to implement focusing. The third group G3 is made up of, in order from the object side, a double-convex positive lens and a positive cemented lens in which a double-convex positive lens and a negative meniscus lens convex on its image plane side are cemented together. The aperture stop S is located between the second group G2 and the third group G3, and remains fixed in front of the third group G3 during focusing. In the rear of the first G1 and the third group G3, there are the plane-parallel plates F1 and located, each a filter for cutting off light having a specific wavelength, for instance, 1,060 nm YAG laser, 810 nm semiconductor laser or light in the near infrared region. An imaging device located near the image plane I of the endoscopic objective optical system is combined with the aforesaid endoscopic objective optical system, providing an imaging optical system. The imaging device has the cover glass G cemented to it for protection of the imaging plane.

Further, the aforesaid high-pixel type imaging device is used as the imaging device so that high-definition images are obtained at the respective object points.

Figure 14A:
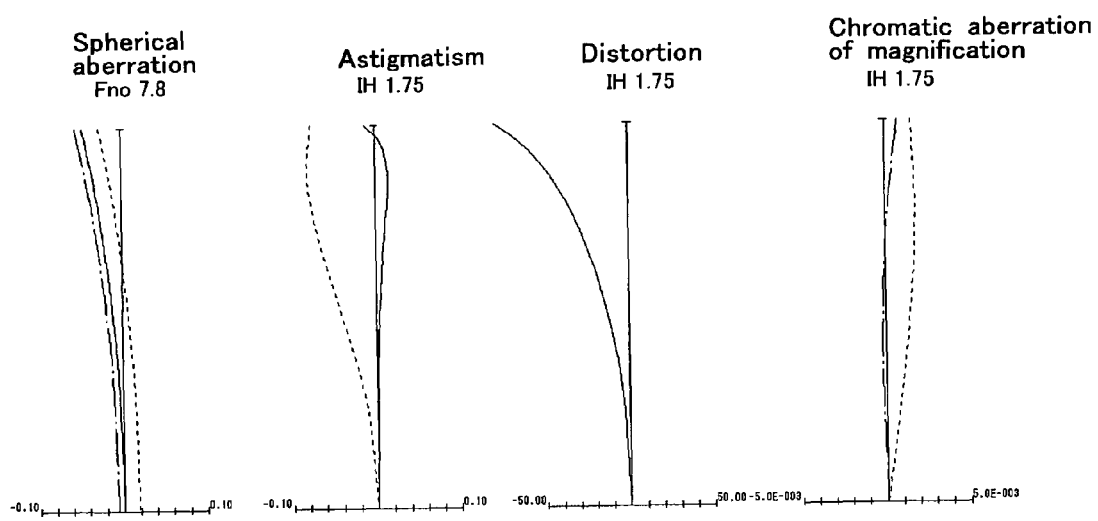
FIG. 14 is aberration curve diagrams for Example 6 upon (a) ordinary viewing and (b) close-up viewing.
Figure 14B:
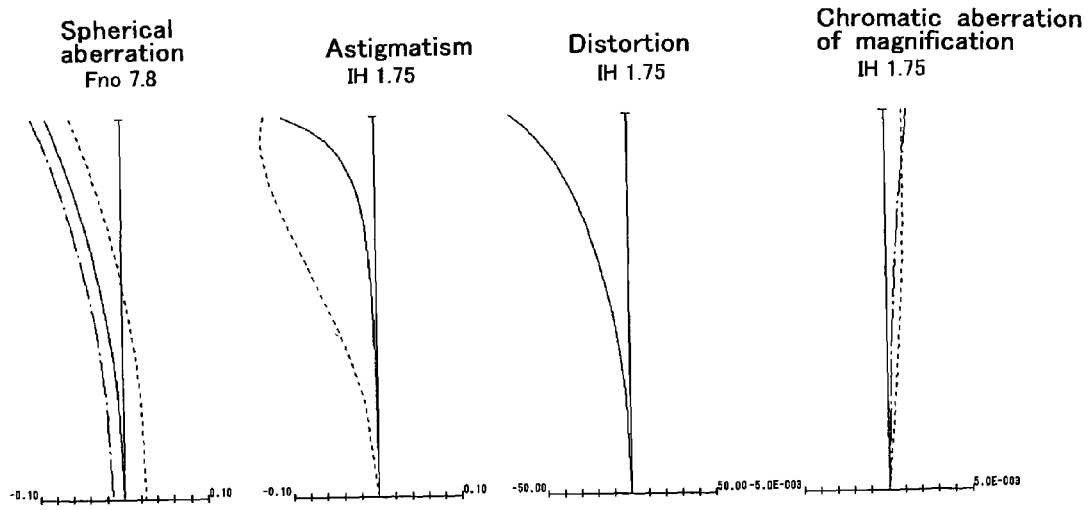

The inventive imaging optical system set up as described above satisfies all Conditions (1) to (11) but (5) and (11). The focal lengths of the first G1, the second G2 and the third group G3 are set at proper values so that the imaging optical system can be made compact without image quality degradation. FIGS. 14(a) and 14(b) are aberration curve diagrams upon (a) ordinary viewing and (b) close-up viewing, respectively.

Example 7

Figure 7A:
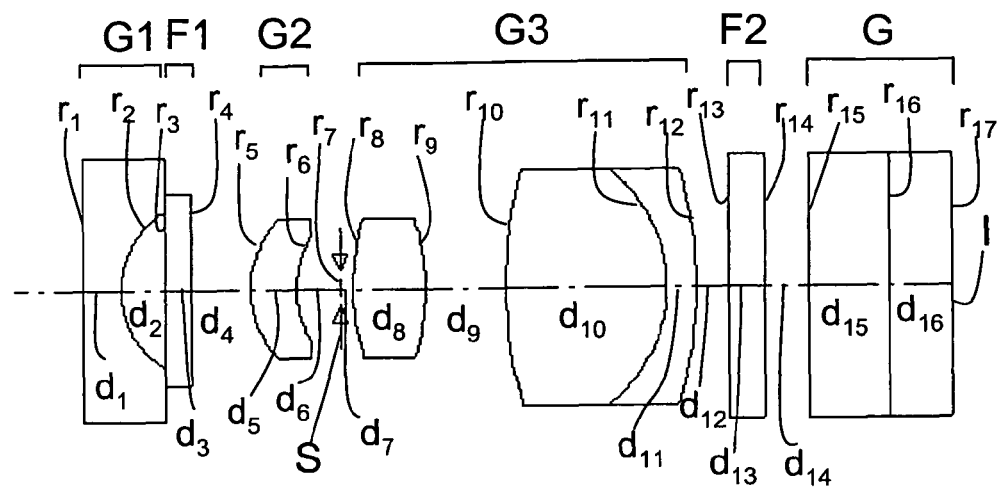
FIG. 7 is illustrative, as in FIG. 1, of the endoscopic objective optical system of Inventive Example 7.
Figure 7B:
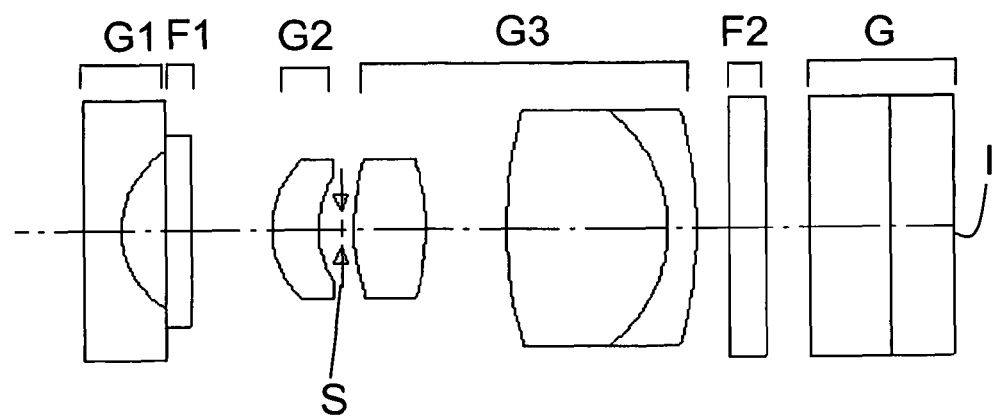

FIG. 7 is a sectional view, as taken through the optical axis, of the construction or arrangement of the endoscopic objective optical system exemplified as Example 7. Lens data on Example 7 will be given later in Table 13. The values of variation parameters in two states: (a) ordinary viewing and (b) close-up viewing will be set out in Table 14.

The optical system shown in FIG. 7 is in two states: (a) ordinary viewing and (b) close-up viewing. The endoscopic objective optical system here is built up of, in order from the object side, the first group G1 of negative refracting power, the second group G2 of positive refracting power, and the third group G3 of positive refracting power. The first group G1 is made up of one plano-concave negative lens. The second group G2 is made up of one positive meniscus lens convex on its object side, and moves on the optical axis to implement focusing. The third group G3 is made up of, in order from the object side, a double-convex positive lens and a positive cemented lens in which a double-convex positive lens and a negative meniscus lens convex on its image plane side are cemented together. The aperture stop S is located between the second group G2 and the third group G3, and remains fixed in front of the third group G3 during focusing. In the rear of the first G1 and the third group G3, there are the plane-parallel plates F1 and F2, each a filter for cutting off light having a specific wavelength, for instance, 1,060 nm YAG laser, 810 nm semiconductor laser or light in the near infrared region. An imaging device located near the image plane I of the endoscopic objective optical system is combined with the aforesaid endoscopic objective optical system, providing an imaging optical system. The imaging device has the cover glass G cemented to it for protection of the imaging plane.

Further, the aforesaid high-pixel type imaging device is used as the imaging device so that high-definition images are obtained at the respective object points.

Figure 15A:
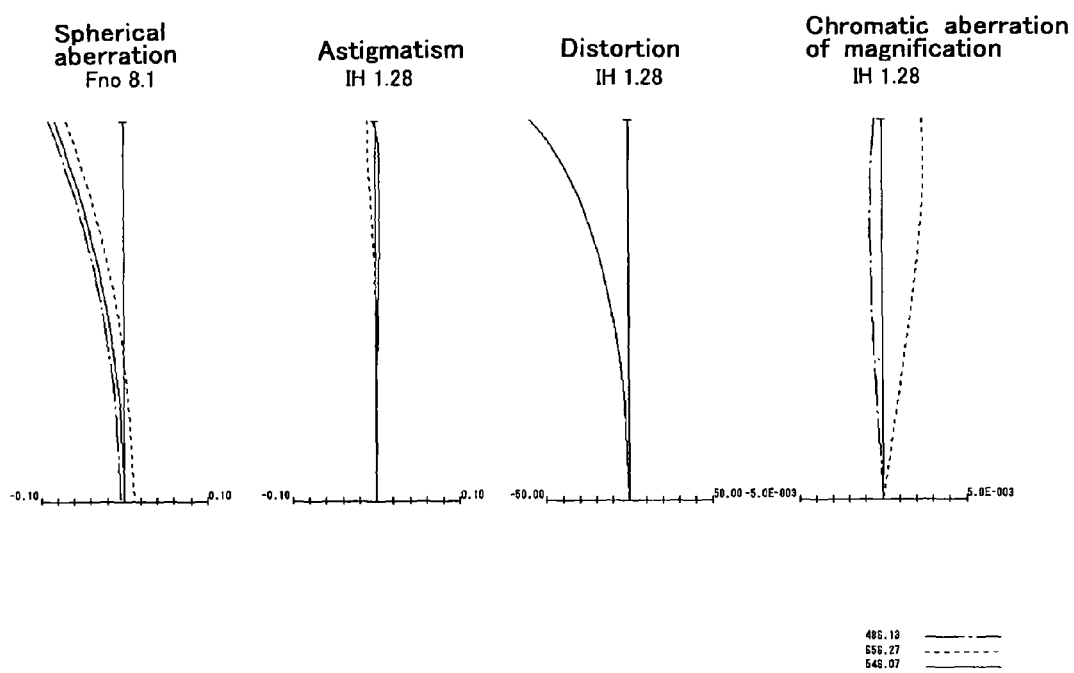
FIG. 15 is aberration curve diagrams for Example 7 upon (a) ordinary viewing and (b) close-up viewing.
Figure 15B:
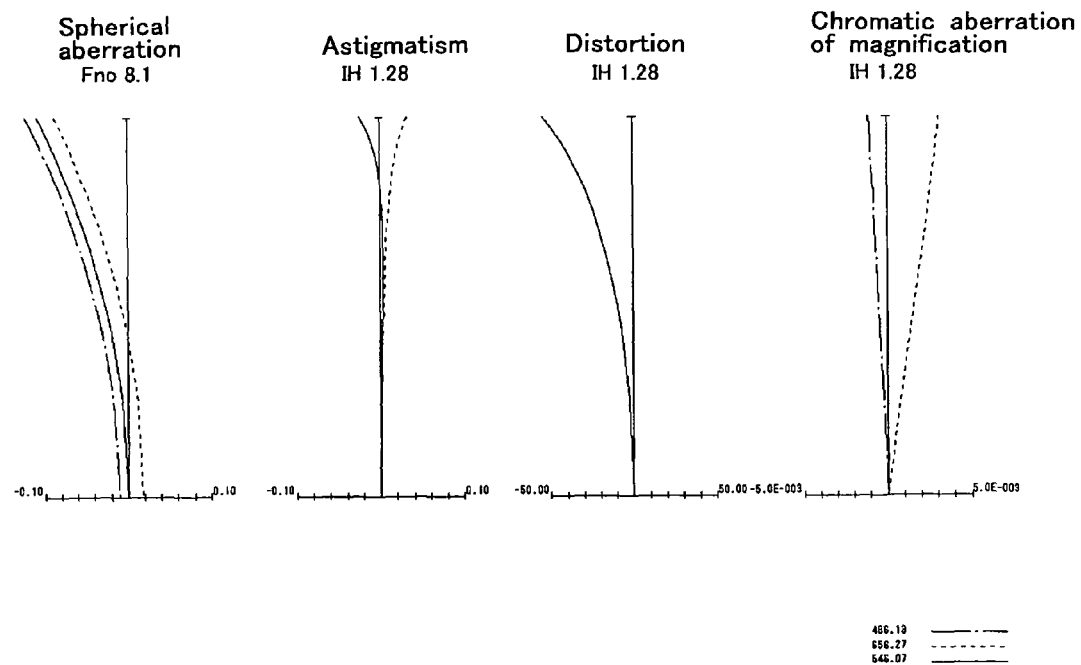

The inventive imaging optical system set up as described above satisfies all Conditions (1) to (11) but (5) and (11). The focal lengths of the first G1, the second G2 and the third group G3 are set at proper values so that the imaging optical system can be made compact without image quality degradation. FIGS. 15(a) and 15(b) are aberration curve diagrams upon (a) ordinary viewing and (b) close-up viewing, respectively.

Example 8

Figure 8A:
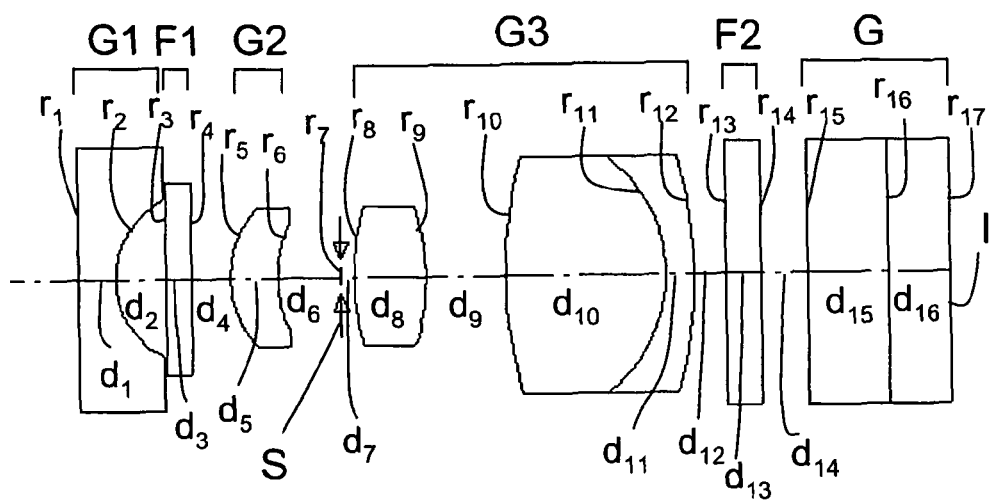
FIG. 8 is illustrative, as in FIG. 1, of the endoscopic objective optical system of Inventive Example 8.
Figure 8B:
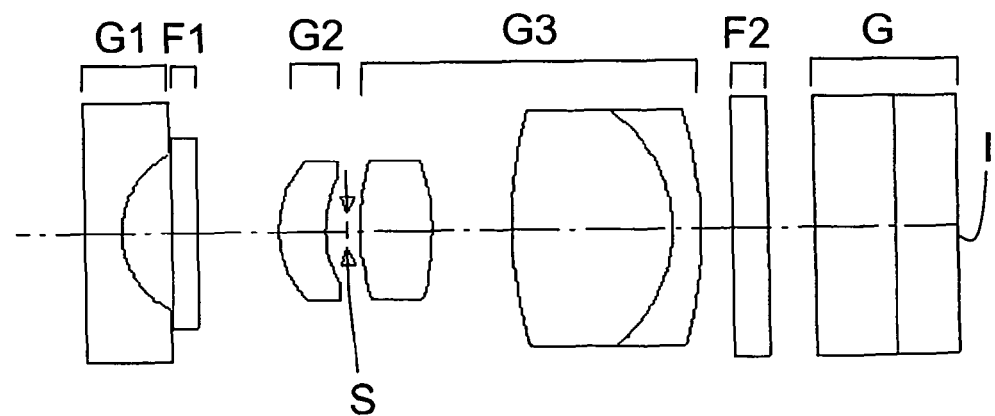

FIG. 8 is a sectional view, as taken through the optical axis, of the construction or arrangement of the endoscopic objective optical system exemplified as Example 8. Lens data on Example 8 will be given later in Table 15. The values of variation parameters in two states: (a) ordinary viewing and (b) close-up viewing will be set out in Table 16.

The optical system shown in FIG. 8 is in two states: (a) ordinary viewing and (b) close-up viewing. The endoscopic objective optical system here is built up of, in order from the object side, the first group G1 of negative refracting power, the second group G2 of positive refracting power, and the third group G3 of positive refracting power. The first group G1 is made up of one plano-concave negative lens. The second group G2 is made up of one positive meniscus lens convex on its object side, and moves on the optical axis to implement focusing. The third group G3 is made up of, in order from the object side, a double-convex positive lens and a positive cemented lens in which a double-convex positive lens and a negative meniscus lens convex on its image plane side are cemented together. The aperture stop S is located between the second group G2 and the third group G3, and remains fixed in front of the third group G3 during focusing. In the rear of the first G1 and the third group G3, there are the plane-parallel plates F1 and F2, each a filter for cutting off light having a specific wavelength, for instance, 1,060 nm YAG laser, 810 nm semiconductor laser or light in the near infrared region. An imaging device located near the image plane I of the endoscopic objective optical system is combined with the aforesaid endoscopic objective optical system, providing an imaging optical system. The imaging device has the cover glass G cemented to it for protection of the imaging plane.

In Example 8, the third group G3 is common in lens arrangement to that in Example 7, and two lenses are interchanged between the first group G1 and the second group G2 so that the focal length is varied and the angle of field becomes wide.

Further, the aforesaid high-pixel type imaging device is used as the imaging device so that high-definition images are obtained at the respective object points.

Figure 16A:
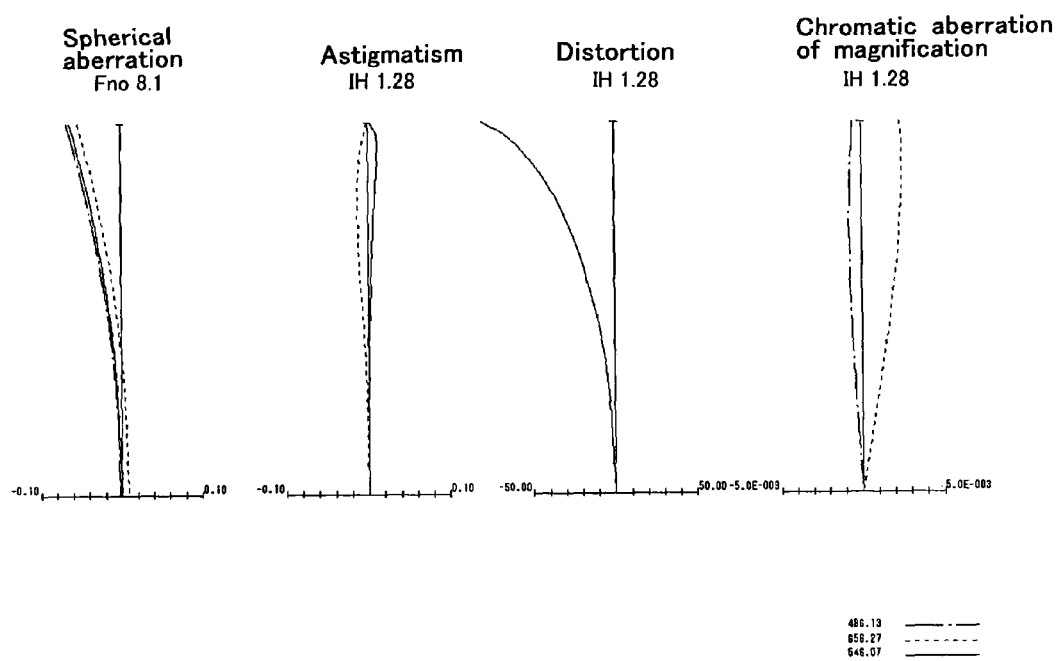
FIG. 16 is aberration curve diagrams for Example 8 upon (a) ordinary viewing and (b) close-up viewing.
Figure 16B:
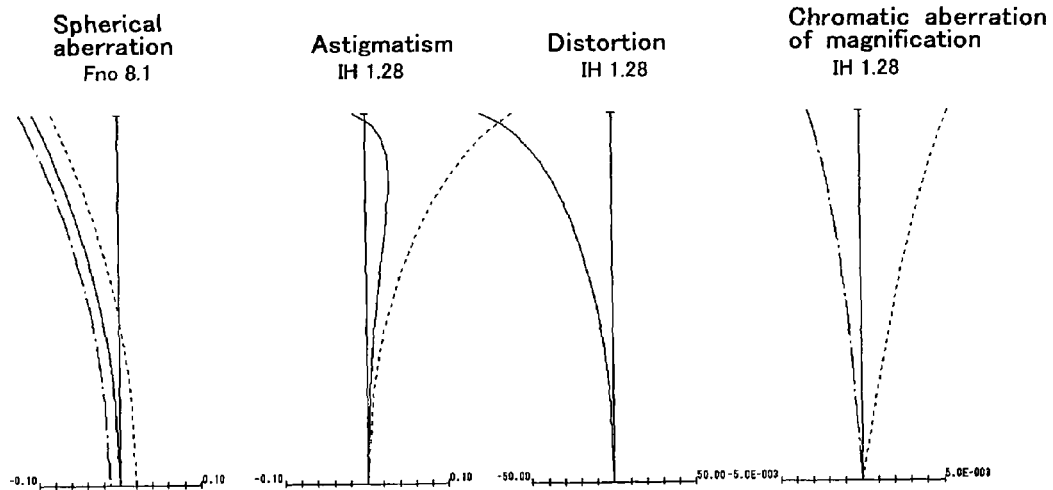

The inventive imaging optical system set up as described above satisfies all Conditions (1) to (11) but (5) and (11). The focal lengths of the first G1, the second G2 and the third group G3 are set at proper values so that the imaging optical system can be made compact without image quality degradation. FIGS. 16(a) and 16(b) are aberration curve diagrams upon (a) ordinary viewing and (b) close-up viewing, respectively.

The numeral data and parameters given in Examples 1 to 8 are set out in the following. Tables 1 to 16. Referring to the symbols referred to hereinafter but not hereinbefore, FD is the focal length (mm), OD the object point distance (mm), F-number the FNo., IH the maximum image height (mm), FP the ordinary viewing, and NP the nearest viewing.

TABLE 1

(Example 1)

| No | r | d | ne | vd |
|---|---|---|---|---|
| 1 | ∞ | 0.32 | 1.88814 | 40.78 |
| 2 | 1.115 | 1.59 | | |

TABLE 1-continued (Example 1)

| No | r | d | ne | vd |
|---|---|---|---|---|
| 3 | −26.666 | 1.21 | 1.77621 | 49.60 |
| 4 | −2.065 | 0.02 | | |
| 5 | 1.662 | 0.28 | 1.77621 | 49.60 |
| 6 | 1.830 | 0.36 | 1.93429 | 18.90 |
| 7 | 1.239 | 0.18 | | |
| 8 (Stop) | ∞ | D8 | | |
| 9 | ∞ | 1.06 | 1.48915 | 70.23 |
| 10 | −1.735 | D10 | | |
| 11 | −1.970 | 0.36 | 1.58482 | 40.75 |
| 12 | −2.281 | 0.07 | | |
| 13 | 4.155 | 1.10 | 1.48915 | 70.23 |
| 14 | −2.021 | 0.32 | 1.93429 | 18.90 |
| 15 | −4.362 | 0.23 | | |
| 16 | ∞ | 0.30 | 1.52498 | 59.89 |
| 17 | ∞ | 0.51 | | |
| 18 | ∞ | 0.75 | 1.51825 | 64.14 |
| 19 | ∞ | 0.49 | 1.50801 | 60.00 |
| 20 (Image Plane) | ∞ | | | |

TABLE 2

(Example 1)

| Parameter | FP | NP |
|---|---|---|
| FD | 1.28 | 1.31 |
| FNo | 6.09 | 6.28 |
| OD | 12.0 | 4.5 |
| D8 | 1.42 | 1.17 |
| D10 | 0.23 | 0.48 |

IH: 1.32 mm

TABLE 3

(Example 2)

| No | r | d | ne | vd |
|---|---|---|---|---|
| 1 | ∞ | 0.32 | 1.88814 | 40.78 |
| 2 | 1.035 | 1.09 | | |
| 3 | −2.902 | 1.37 | 1.77621 | 49.60 |
| 4 | −2.667 | 0.03 | | |
| 5 | 3.461 | 0.90 | 1.74435 | 52.64 |
| 6 | −4.010 | 0.09 | | |
| 7 | 1.690 | 0.31 | 1.85504 | 23.78 |
| 8 | 1.137 | 0.08 | | |
| 9 (Stop) | ∞ | D9 | | |
| 10 | −3.617 | 0.32 | 1.48915 | 70.23 |
| 11 | −1.815 | D11 | | |
| 12 | 4.730 | 0.32 | 1.93429 | 18.90 |
| 13 | 2.400 | 1.63 | 1.48915 | 70.23 |
| 14 | −1.919 | 0.34 | 1.70442 | 30.13 |
| 15 | −2.988 | 0.15 | | |
| 16 | ∞ | 0.30 | 1.52498 | 59.89 |
| 17 | ∞ | 0.51 | | |
| 18 | ∞ | 0.75 | 1.51825 | 64.14 |
| 19 | ∞ | 0.50 | 1.50801 | 60.00 |
| 20 (Image Plane) | ∞ | | | |

TABLE 4

(Example 2)

| Parameter | FP | NP |
|---|---|---|
| FD | 1.29 | 1.30 |
| FNo | 6.50 | 6.68 |
| OD | 12.5 | 4.5 |

TABLE 4-continued (Example 2)

| Parameter | FP | NP |
|---|---|---|
| D9 | 0.70 | 0.31 |
| D11 | 0.35 | 0.74 |

IH: 1.32 mm

TABLE 5

(Example 3)

| No | r | d | ne | vd |
|---|---|---|---|---|
| 1 | ∞ | 0.32 | 1.88814 | 40.78 |
| 2 | 0.995 | 0.51 | | |
| 3 | ∞ | 0.30 | 1.51825 | 64.14 |
| 4 | ∞ | 0.96 | | |
| 5 | 9.465 | 0.52 | 1.77621 | 49.60 |
| 6 | −0.900 | 0.66 | 1.85504 | 23.78 |
| 7 | −1.411 | 0.08 | | |
| 8 | −1.362 | 0.32 | 1.74435 | 52.64 |
| 9 | −2.248 | 0.02 | | |
| 10 | 0.917 | 0.28 | 1.85504 | 23.78 |
| 11 | 0.715 | 0.35 | | |
| 12 (Stop) | ∞ | D12 | | |
| 13 | 4.535 | 0.77 | 1.48915 | 70.23 |
| 14 | −1.590 | D14 | | |
| 15 | −22.772 | 0.32 | 1.93429 | 18.90 |
| 16 | 2.302 | 1.45 | 1.48915 | 70.23 |
| 17 | −2.273 | 0.19 | | |
| 18 | −1.834 | 0.24 | 1.70442 | 30.13 |
| 19 | −2.414 | 0.15 | | |
| 20 | ∞ | 0.30 | 1.52498 | 59.89 |
| 21 | ∞ | 0.51 | | |
| 22 | ∞ | 0.75 | 1.51825 | 64.14 |
| 23 | ∞ | 0.50 | 1.50801 | 60.00 |
| 24 (Image Plane) | ∞ | | | |

TABLE 6

(Example 3)

| Parameter | FP | NP |
|---|---|---|
| FD | 1.30 | 1.28 |
| FNo | 7.65 | 7.79 |
| OD | 15.0 | 5.0 |
| D12 | 0.86 | 0.76 |
| D14 | 0.34 | 0.44 |

IH: 1.32 mm

TABLE 7

(Example 4)

| No | r | d | ne | vd |
|---|---|---|---|---|
| 1 | ∞ | 0.45 | 1.88814 | 40.78 |
| 2 | 2.000 | 0.86 | | |
| 3 | 2.799 | 0.27 | 1.77621 | 49.60 |
| 4 | 0.995 | 0.28 | | |
| 5 | ∞ | 0.30 | 1.52498 | 59.89 |
| 6 | ∞ | 0.02 | | |
| 7 | 5.869 | 0.34 | 1.73234 | 54.68 |
| 8 | −5.869 | 0.21 | 1.85504 | 23.78 |
| 9 | −7.222 | 0.14 | | |
| 10 | 3.341 | 1.22 | 1.85504 | 23.78 |
| 11 | 1.425 | D11 | | |
| 12 | 3.024 | 0.70 | 1.77621 | 49.60 |
| 13 | −1.505 | 0.20 | | |
| 14 (Stop) | ∞ | D14 | | |
| 15 | 32.030 | 0.20 | 1.77621 | 49.60 |

TABLE 7-continued (Example 4)

| No | r | d | ne | vd |
|---|---|---|---|---|
| 16 | 2.664 | 0.29 | | |
| 17 | 2.161 | 0.96 | 1.73234 | 54.68 |
| 18 | −2.794 | 0.28 | 1.85504 | 23.78 |
| 19 | 9.518 | 0.20 | | |
| 20 | ∞ | 0.40 | 1.51564 | 75.00 |
| 21 | ∞ | 0.28 | | |
| 22 | ∞ | 0.80 | 1.51825 | 64.14 |
| 23 | ∞ | 0.55 | 1.61379 | 50.20 |
| 24 (Image Plane) | ∞ | | | |

TABLE 8

(Example 4)

| Parameter | FP | NP |
|---|---|---|
| FD | 1.46 | 1.37 |
| FNo | 7.76 | 7.74 |
| OD | 15.0 | 5.2 |
| D11 | 0.20 | 0.24 |
| D14 | 1.52 | 1.48 |

IH: 1.32 mm

TABLE 9

(Example 5)

| No | r | d | ne | vd |
|---|---|---|---|---|
| 1 | ∞ | 0.42 | 1.88814 | 40.78 |
| 2 | 1.475 | 0.65 | | |
| 3 | ∞ | 0.30 | 1.52498 | 59.89 |
| 4 | ∞ | 0.05 | | |
| 5 | 3.850 | 0.64 | 1.73234 | 54.68 |
| 6 | −3.700 | 0.25 | | |
| 7 | −3.067 | 0.34 | 1.77621 | 49.60 |
| 8 | 4.121 | 0.33 | 1.85504 | 23.78 |
| 9 | 5.780 | D9 | | |
| 10 | 1.998 | 0.55 | 1.77621 | 49.60 |
| 11 | 7.369 | 0.77 | | |
| 12 (Stop) | ∞ | D12 | | |
| 13 | 5.267 | 1.03 | 1.77621 | 49.60 |
| 14 | 95.318 | 0.69 | | |
| 15 | 2.536 | 1.41 | 1.73234 | 54.68 |
| 16 | −2.309 | 0.28 | 1.85504 | 23.78 |
| 17 | 190.963 | 0.30 | | |
| 18 | ∞ | 0.40 | 1.51564 | 75.00 |
| 19 | ∞ | 0.50 | | |
| 20 | ∞ | 0.75 | 1.51825 | 64.14 |
| 21 | ∞ | 0.55 | 1.61379 | 50.20 |
| 22 (Image Plane) | ∞ | | | |

TABLE 10

(Example 5)

| Parameter | FP | NP |
|---|---|---|
| FD | 1.62 | 1.52 |
| FNo | 6.56 | 6.62 |
| OD | 12.0 | 5.4 |
| D9 | 0.18 | 0.35 |
| D12 | 0.32 | 0.15 |

IH: 1.32 mm

TABLE 11

(Example 6)

| No | r | d | ne | vd |
|---|---|---|---|---|
| 1 | 17.836 | 0.45 | 1.88814 | 40.78 |
| 2 | 1.061 | 0.71 | | |
| 3 | ∞ | 0.30 | 1.51564 | 75.00 |
| 4 | ∞ | D4 | | |
| 5 | 1.423 | 0.46 | 1.59911 | 39.24 |
| 6 | 1.676 | D6 | | |
| 7 (Stop) | ∞ | 0.24 | | |
| 8 | 7.800 | 0.94 | 1.77621 | 49.60 |
| 9 | −3.339 | 1.18 | | |
| 10 | 3.041 | 1.51 | 1.48915 | 70.23 |
| 11 | −2.041 | 0.39 | 1.93430 | 18.90 |
| 12 | −5.339 | 0.58 | | |
| 13 | ∞ | 0.40 | 1.52498 | 59.89 |
| 14 | ∞ | 1.42 | | |
| 15 | ∞ | 0.80 | 1.51825 | 64.14 |
| 16 | ∞ | 0.65 | 1.50801 | 60.00 |
| 17 (Image Plane) | ∞ | | | |

TABLE 12

(Example 6)

| Parameter | FP | NP |
|---|---|---|
| FD | 1.68 | 1.64 |
| FNo | 7.78 | 7.81 |
| OD | 11.0 | 4.8 |
| D4 | 0.28 | 0.67 |
| D6 | 0.91 | 0.52 |

IH: 1.754 mm

TABLE 13

(Example 7)

| No | r | d | ne | vd |
|---|---|---|---|---|
| 1 | ∞ | 0.42 | 1.88814 | 40.78 |
| 2 | 1.064 | 0.50 | | |
| 3 | ∞ | 0.30 | 1.52498 | 59.89 |
| 4 | ∞ | D4 | | |
| 5 | 1.142 | 0.52 | 1.88814 | 40.78 |
| 6 | 1.225 | D6 | | |
| 7 (Stop) | ∞ | 0.15 | | |
| 8 | 2.787 | 0.80 | 1.48915 | 70.23 |
| 9 | −2.787 | 0.90 | | |
| 10 | 4.922 | 1.80 | 1.77621 | 49.60 |
| 11 | −1.703 | 0.32 | 1.93430 | 18.90 |
| 12 | −4.834 | 0.36 | | |
| 13 | ∞ | 0.40 | 1.51564 | 75.00 |
| 14 | ∞ | 0.50 | | |
| 15 | ∞ | 0.90 | 1.51825 | 64.14 |
| 16 | ∞ | 0.70 | 1.61379 | 50.20 |
| 17 (Image Plane) | ∞ | | | |

TABLE 14

(Example 7)

| Parameter | FP | NP |
|---|---|---|
| FD | 1.38 | 1.34 |
| FNo | 8.07 | 8.05 |
| OD | 11.0 | 5.0 |
| D4 | 0.66 | 0.90 |
| D6 | 0.48 | 0.24 |

IH: 1.284 mm

TABLE 15

(Example 8)

| No | r | d | ne | vd |
|---|---|---|---|---|
| 1 | ∞ | 0.42 | 1.88814 | 40.78 |
| 2 | 1.009 | 0.56 | | |
| 3 | ∞ | 0.30 | 1.52498 | 59.89 |
| 4 | ∞ | D4 | | |
| 5 | 1.173 | 0.52 | 1.88814 | 40.78 |
| 6 | 1.305 | D6 | | |
| 7 (Stop) | ∞ | 0.15 | | |
| 8 | 2.787 | 0.80 | 1.48915 | 70.23 |
| 9 | −2.787 | 0.90 | | |
| 10 | 4.922 | 1.80 | 1.77621 | 49.60 |
| 11 | −1.703 | 0.32 | 1.93430 | 18.90 |
| 12 | −4.834 | 0.36 | | |
| 13 | ∞ | 0.40 | 1.51564 | 75.00 |
| 14 | ∞ | 0.50 | | |
| 15 | ∞ | 0.90 | 1.51825 | 64.14 |
| 16 | ∞ | 0.70 | 1.61379 | 50.20 |
| 17 (Image Plane) | ∞ | | | |

TABLE 16

(Example 8)

| Parameter | FP | NP |
|---|---|---|
| FD | 1.32 | 1.25 |
| FNo | 8.08 | 7.87 |
| OD | 13.5 | 5.0 |
| D4 | 0.43 | 0.90 |
| D6 | 0.71 | 0.24 |

IH: 1.284 mm

Set out in Table 17 are the values of Conditions (1) to (11) in Examples 1 to 8.

TABLE 17

| | Example | | | | | | | |
|---|---|---|---|---|---|---|---|---|
| Condition | 1 | 2 | 3 | 4 | 5 | 6 | 7 | 8 |
| (1)-1 | 67.8 | 68.1 | 72.9 | 62.6 | 64.4 | 80.4 | 67.3 | 80.8 |
| (1)-2 | 64.7 | 65.8 | 69.3 | 65.8 | 65.9 | 77.0 | 65.9 | 74.6 |
| (2) | 0.95 | 0.97 | 0.95 | 1.05 | 1.02 | 0.96 | 0.98 | 0.92 |
| (3) | 1.02 | 1.01 | 0.99 | 0.94 | 0.94 | 0.97 | 0.97 | 0.94 |
| (4) | 0.36 | 0.84 | −0.16 | −0.05 | 1.18 | 3.66 | 2.08 | 2.00 |
| (5) | 0.36 | 0.84 | −0.16 | −0.05 | 1.18 | 3.66 | 2.08 | 2.00 |
| (6) | 5.80 | 0.66 | 5.21 | −0.47 | −0.47 | −0.14 | −0.25 | −0.25 |
| (7) | 0.48 | 1.80 | −1.18 | 40.02 | −1.81 | −1.99 | −1.93 | −2.02 |
| (8) | 16.02 | 3.08 | 10.08 | −0.45 | −0.98 | −0.76 | −0.87 | −0.86 |
| (9) | 0.84 | 0.88 | 0.88 | 1.11 | 1.05 | 0.93 | 0.94 | 0.88 |
| (10) | 0.19 | 0.30 | 0.08 | 0.03 | 0.10 | 0.23 | 0.17 | 0.35 |
| (11) | 0.44 | 0.10 | 0.66 | — | 0.62 | — | — | — |

For instance, the objective optical system of the invention may be embodied as follows.

[1] An objective optical system, characterized in that focusing can be implemented relative to an object point distance by movement of at least one lens group, with satisfaction of the following Conditions (1)-1, (1)-2 and (2):

$$\omega f > 60 \quad (1)\text{-}1$$

$$\omega n > 60 \quad (1)\text{-}2$$

$$0.8 < \omega n/\omega f < 1.2 \quad (2)$$

where $\omega f$ is the maximum half angle of view (°) upon viewing at a far distance object point, and $\omega n$ is the maximum half angle of view (°) upon close-up viewing.

[2] An objective optical system, characterized by comprising at least three lens groups, at least one of which moves to implement focusing relative to an object point distance change, with satisfaction of the following Conditions (1)-1 and (1)-2:

$$\omega f > 60 \quad (1)\text{-}1$$

$$\omega n > 60 \quad (1)\text{-}2$$

where $\omega f$ is the maximum half angle of view (°) upon viewing at a far distance object point, and $\omega n$ is the maximum half angle of view (°) upon close-up viewing.

[3] An objective optical system, characterized by comprising at least three lens groups, at least one of which moves to implement focusing relative to an object point distance change, with satisfaction of the following Condition (2):

$$0.8 < \omega n/\omega f < 1.2 \quad (2)$$

where $\omega f$ is the maximum half angle of view (°) upon viewing at a far distance object point, and $\omega n$ is the maximum half angle of view (°) upon close-up viewing.

[4] The objective optical system according to any one of [1] to [3], characterized in that the moving group is the second group of positive power.

[5] The objective optical system according to any one of [1] to [4], characterized by satisfying the following Condition (3):

$$0.85 < fn/ff < 1.15 \quad (3)$$

where $fn$ is the focal length of the whole system upon viewing at a near distance, and $ff$ is the focal length of the whole system upon viewing at a far distance.

[6] The objective optical system according to any one of [1] to [5], characterized by comprising, in order from the object side, a first group of positive power, a second group of positive power and a third group of positive power.

[7] The objective optical system according to any one of [1] to [5], characterized by comprising, in order from the object side, a first group of positive power, a second group of positive power and a third group of negative power.

[8] The objective optical system according to any one of [1] to [5], characterized by comprising, in order from the object side, a first group of negative power, a second group of positive power and a third group of positive power.

[9] The objective optical system according to any one of [1] to [5], characterized by comprising, in order from the object side, a first group of negative power, a second group of positive power and a third group of negative power.

[10] An objective optical system, characterized by comprising, in order from the object side, a first group of negative power, a second group of positive power and a third group of positive power, wherein in association with an object point distance change from a far distance object point to a near distance object point, the second group moves toward the image side for focusing, with satisfaction of the following Condition (3):

$$0.85 < fn/ff < 1.15 \quad (3)$$

where $fn$ is the focal length of the whole system upon viewing at a near distance, and ff is the focal length of the whole system upon viewing at a far distance.

[11] The objective optical system according to any one of [1] to [6], [8] and [10], characterized in that the third group is a group of positive power, with satisfaction of the following Condition (4):

$$0.3 < f_2/f_3 < 6 \quad (4)$$

where
 $f_2$ is the focal length of the second group, and
 $f_3$ is the focal length of the third group.

[12] The objective optical system according to [11], characterized by satisfying the following Condition (4):

$$0.6 < f_2/f_3 < 4 \quad (4)$$

[13] The objective optical system according to any one of [1] to [5], [7] and [9], characterized in that the third group is a group of negative power, with satisfaction of the following Condition (5):

$$-0.25 < f_2/f_3 < 0 \quad (5)$$

where
 $f_2$ is the focal length of the second group, and
 $f_3$ is the focal length of the third group.

[14] The objective optical system according to any one of [1] to [5] and [8] to [13], characterized in that the first group is a group of negative power, with satisfaction of the following Condition (6):

$$-0.6 < f_1/f_2 < -0.1 \quad (6)$$

where
 $f_1$ is the focal length of the first group, and
 $f_2$ is the focal length of the second group.

[15] The objective optical system according to any one of [1] to [5], [7], [8] and [10] to [14], characterized by satisfying the following Condition (7):

$$-2.4 < f_3/f_1 < -1.5 \quad (7)$$

where
 $f_1$ is the focal length of the first group, and
 $f_3$ is the focal length of the third group.

[16] The objective optical system according to any one of [1] to [5] and [8] to [15], characterized in that the first group consists of one negative lens concave on its image side.

[17] The objective optical system according to [16], characterized in that the negative lens in the first group has a plane on its object side.

[18] The objective optical system according to any one of [1] to [17], characterized in that the second group is made up of a positive meniscus lens convex on its object side.

[19] The objective optical system according to any one of [1] to [6], [8], [10] to [12] and [14] to [18], characterized in that the third group is made up of a double-convex positive lens and a positive cemented lens in which a positive lens and a negative lens are cemented together.

[20] The objective optical system according to any one of [1] to [5] and [8] to [19], characterized by satisfying the following Condition (8):

$$-1.2 < f_1/f\!f < -0.6 \quad (8)$$

where
 $f_1$ is the focal length of the first group, and
 ff is the focal length of the whole system upon viewing at a far distance.

[21] The objective optical system according to any one of [1] to [20], characterized by satisfying the following Condition (3):

$$0.9 < f_n/f\!f < 1.1 \quad (3)$$

where
 fn is the focal length of the whole system upon viewing at a near distance, and
 ff is the focal length of the whole system upon viewing at a far distance.

[22] The objective optical system according to any one of [1] to [21], characterized by satisfying the following Condition (9):

$$0.8 < DTLn \times f\!f / DTLf \times fn < 1.2 \quad (9)$$

where
 DTLn is distortion at the maximum image height upon viewing at a near distance, and
 DTLf is distortion at the maximum image height upon viewing at a far distance.

[23] The objective optical system according to any one of [3] to [22], characterized by satisfying the following Conditions (1)-1 and (1)-2:

$$\omega f > 60 \quad (1)\text{-}1$$

$$\omega n > 60 \quad (1)\text{-}2$$

where
 $\omega f$ is the maximum half angle of view (°) upon viewing at a far distance object point, and
 $\omega n$ is the maximum half angle of view (°) upon close-up viewing.

[24] The objective optical system according to any one of [2] and [4] to [23], characterized by satisfying the following Condition (2):

$$0.8 < \omega n/\omega f < 1.2 \quad (2)$$

where
 $\omega f$ is the maximum half angle of view (°) upon viewing at a far distance object point, and
 $\omega n$ is the maximum half angle of view (°) upon close-up viewing.

[25] The objective optical system according to any one of [1] to [24], characterized by satisfying the following Condition (2):

$$0.9 < \omega n/\omega f < 1.1 \quad (2)$$

where
 $\omega f$ is the maximum half angle of view (°) upon viewing at a far distance object point, and
 $\omega n$ is the maximum half angle of view (°) upon close-up viewing.

[26] The objective optical system according to any one of [1] to [25], characterized by satisfying the following Condition (10):

$$0.07 < \Delta d/f\!f < 0.38 \quad (10)$$

where
 $\Delta d$ is the amount of movement of the lens in the moving group upon focusing from a far distance object point to a near distance object point, and
 ff is the focal length of the whole optical system upon viewing at a far distance.

[27] The objective optical system according to any one of [1] to [26], characterized in that a stop is positioned in front of the third group, and remains fixed during focusing.

[28] The objective optical system according to any one of [1] to [27], characterized by being used on or with an endoscope.

INDUSTRIAL APPLICABILITY

The present invention can provide a high-performance objective lens that enables focusing to be implemented relative to an object point distance change with no or little angle-of-view change, and is well compatible with a high-pixel type imaging device.

| EXPLANATION OF REFERENCES IN THE DRAWINGS | |
|---|---|
| G1: | the first group, |
| G2: | the second group, |
| G3: | the third group, |
| S: | aperture stop, |
| F1, F2: | plane-parallel plate, |
| G: | cover glass, and |
| I: | image plane. |

What we claim is:

1. An objective optical system, characterized by comprising, in order from an object side thereof, a first group of negative power, a second group of positive power, an aperture stop, and a third group of positive power, wherein:

only said second group moves thereby implementing focusing relative to an object point distance change, and the following conditions are satisfied:

$$\omega f > 60 \quad (1)\text{-}1$$

$$\omega n > 60 \quad (1)\text{-}2$$

$$1.2 < f1/f\!f < -0.6 \quad (8)$$

where $\omega f$ is a maximum half angle of view (°) upon viewing at a far distance, $\omega n$ is a maximum half angle of view (°) upon viewing at a near distance, f1 is a focal length of said first lens group, and ff is a focal length of the whole system upon viewing at a far distance.

* * * * *